US010433553B2

(12) United States Patent
Köhn et al.

(10) Patent No.: US 10,433,553 B2
(45) Date of Patent: Oct. 8, 2019

(54) SALTS OF N-(1,3,4-OXADIAZOL-2-YL) ARYL CARBOXYLIC ACID AMIDES AND THE USE OF SAME AS HERBICIDES

(71) Applicant: BAYER CROPSCIENCE AKTIENGESELLSCHAFT, Monheim am Rhein (DE)

(72) Inventors: Arnim Köhn, Klein-Winternheim (DE); Ralf Braun, Ramberg (DE); Hartmut Ahrens, Egelsbach (DE); Christian Waldraff, Bad Vilbel (DE); Ines Heinemann, Hofheim (DE); Hansjörg Dietrich, Liederbach am Taunus (DE); Elmar Gatzweiler, Bad Nauheim (DE); Christopher Hugh Rosinger, Hofheim (DE)

(73) Assignee: BAYER CROPSCIENCE AKTIENGESELLSCHAFT, Monhem am Rhein (DE)

( * ) Notice: Subject to any disclaimer, the term of this patent is extended or adjusted under 35 U.S.C. 154(b) by 53 days.

(21) Appl. No.: 15/558,832

(22) PCT Filed: Mar. 14, 2016

(86) PCT No.: PCT/EP2016/055396
§ 371 (c)(1),
(2) Date: Sep. 15, 2017

(87) PCT Pub. No.: WO2016/146561
PCT Pub. Date: Sep. 22, 2016

(65) Prior Publication Data

US 2018/0077935 A1 Mar. 22, 2018

(30) Foreign Application Priority Data

Mar. 17, 2015 (EP) .................................... 15159483

(51) Int. Cl.
*A01N 43/82* (2006.01)
*C07D 271/113* (2006.01)
*C07D 413/12* (2006.01)

(52) U.S. Cl.
CPC .......... *A01N 43/82* (2013.01); *C07D 271/113* (2013.01); *C07D 413/12* (2013.01)

(58) Field of Classification Search
None
See application file for complete search history.

(56) References Cited

U.S. PATENT DOCUMENTS

| | | | |
|---|---|---|---|
| 4,416,683 A | 11/1983 | Burow, Jr. |
| 2014/0080705 A1 | 3/2014 | Koeehn et al. |
| 2015/0031537 A1 | 1/2015 | Dörner-Rieping et al. |
| 2015/0105253 A1 | 4/2015 | Braun et al. |

FOREIGN PATENT DOCUMENTS

| | | |
|---|---|---|
| WO | 2012/126932 A1 | 9/2012 |
| WO | 2013/124245 A1 | 8/2013 |
| WO | 2013/164331 A1 | 11/2013 |

OTHER PUBLICATIONS

Anonym: "Data of comparative experiments 13719550.9-1462" (Jul. 9, 2015), Available at: URL:https://register.epo.org/application?documentid=EXQ5465S2290F14&number=EP13719550&lng=en&npl=true, pp. 1-5.
International Search Report of PCT/EP2016/055396 dated May 11, 2016.

*Primary Examiner* — John Pak
*Assistant Examiner* — Daniel L Branson
(74) *Attorney, Agent, or Firm* — McBee Moore Woodward & Vanik IP, LLC

(57) ABSTRACT

Salts of N-(1,3,4-oxadiazol-2-yl)arylcarboxamides of the general formula (I) are described as herbicides.

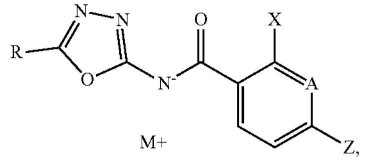

(I)

In this formula (I), X, Z and R are radicals such as hydrogen, organic radicals such as alkyl, and other radicals such as halogen. A is nitrogen or carbon. $M^+$ is a cation.

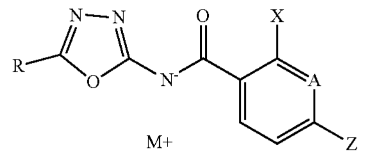

(I)

17 Claims, No Drawings

SALTS OF N-(1,3,4-OXADIAZOL-2-YL) ARYL CARBOXYLIC ACID AMIDES AND THE USE OF SAME AS HERBICIDES

CROSS REFERENCE TO RELATED APPLICATIONS

This application is a § 371 National State Application of PCT/EP2016/055396, filed Mar. 14, 2016, which claims priority to European Application No. 15159483.5 filed Mar. 17, 2015.

BACKGROUND OF THE INVENTION

Field of the Invention

The invention relates to the technical field of the herbicides, especially that of the herbicides for selective control of broad-leaved weeds and weed grasses in crops of useful plants.

Description of Related Art

WO 2012/126932 A1 describes N-(1,3,4-oxadiazol-2-yl) benzamides and use thereof as herbicides. The active ingredients described therein do not always exhibit sufficient activity against harmful plants and/or some do not have sufficient compatibility with some important crop plants such as cereal species, corn and rice. It is therefore an object of the present invention to provide further herbicidally active ingredients. This object is achieved by the inventive salts of N-(1,3,4-oxadiazol-2-yl)arylcarboxamides that are described hereinafter.

SUMMARY

The present invention thus provides salts of N-(1,3,4-oxadiazol-2-yl)benzamides of the formula (I)

(I)

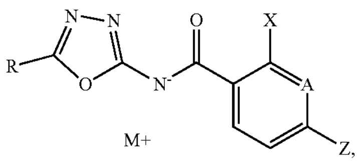

in which

A is N or CY,

R is hydrogen, $(C_1-C_6)$-alkyl, $R^1O$—$(C_1-C_6)$-alkyl, $CH_2R^6$, $(C_3-C_7)$-cycloalkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $OR^1$, $NHR^1$, methoxycarbonyl, ethoxycarbonyl, methoxycarbonylmethyl, ethoxycarbonylmethyl, methylcarbonyl, trifluoromethylcarbonyl, dimethylamino, acetylamino, methylsulfenyl, methylsulfinyl, methylsulfonyl, or heteroaryl, heterocyclyl, benzyl or phenyl each substituted by s radicals from the group of halogen, nitro, cyano, $(C_1-C_6)$-alkyl, halo-$(C_1-C_6)$-alkyl, $(C_3-C_6)$-cycloalkyl, $S(O)_n$ —$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl, X is nitro, halogen, cyano, formyl, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $NR_1R_2$, $P(O)(OR^5)_2$, $CH_2P(O)(OR^5)_2$, $(C_1-C_6)$-alkylheteroaryl, $(C_1-C_6)$-alkylheterocyclyl, where the two latter radicals are each substituted by s halogen, $(C_1-C_6)$-alkyl, halo-$(C_1-C_6)$-alkyl, $S(O)_n$—$(C_1-C_6)$-alkyl, $(C_1-C_6)$-alkoxy, halo-$(C_1-C_6)$-alkoxy radicals, and where heterocyclyl bears n oxo groups, Y is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $CO(NOR^1)R^1$, $NR^1SO_2R^2$, $NR^1COR^1$, $OR^1$, $OSO_2R^2$, $S(O)_nR^2$, $SO_2OR^1$, $SO_2N(R^1)_2$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-OSO2$R^2$, $(C_1-C_6)$-alkyl-$CO_2R^1$, $(C_1-C_6)$-alkyl-CN, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, $CH_2P(O)(OR^5)_2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the 6 latter radicals are each substituted by s radicals from the group of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl bears n oxo groups, Z is halogen, cyano, thiocyanato, $(C_1-C_6)$-alkyl, $(C_1-C_6)$-alkoxy, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, heteroaryl, heterocyclyl or phenyl, where the three latter radicals are each substituted by s radicals from the group of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy or halo-$(C_1-C_6)$-alkoxy, and where heterocyclyl bears n oxo groups, or Z may also be hydrogen if Y is the $S(O)_nR^2$ radical, $R^1$ is hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where the 21 latter radicals are substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and $(C_1-C_4)$-alkoxy-$(C_2-C_6)$-alkoxycarbonyl, and where heterocyclyl bears n oxo groups, $R^2$ is ($C_1$-$C_6$)-alkyl, ($C_1$-$C_6$)-haloalkyl, ($C_2$-$C_6$)-alkenyl, ($C_2$-$C_6$)-haloalkenyl, ($C_2$-$C_6$)-alkynyl, ($C_2$-$C_6$)-haloalkynyl, ($C_3$-$C_6$)-cycloalkyl, ($C_3$-$C_6$)-cycloalkenyl, ($C_3$-$C_6$)-halocycloalkyl, ($C_1$-$C_6$)-alkyl-O—($C_1$-$C_6$)-alkyl, ($C_3$-$C_6$)-cycloalkyl-($C_1$-$C_6$)-alkyl, phenyl, phenyl-($C_1$-$C_6$)-alkyl, heteroaryl, ($C_1$-$C_6$)-alkylheteroaryl, heterocyclyl, ($C_1$-$C_6$)-alkylheterocyclyl, ($C_1$-$C_6$)-alkyl-O-heteroaryl, ($C_1$-$C_6$)-alkyl-O-heterocyclyl, ($C_1$-$C_6$)-alkyl-$NR^3$-heteroaryl, ($C_1$-$C_6$)-alkyl-$NR^3$-heterocyclyl, where the 21 latter radicals are substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and ($C_1$-$C_4$)-alkoxy-($C_2$-$C_6$)-alkoxycarbonyl, and where heterocyclyl bears n oxo groups, $R^3$ is hydrogen, ($C_1$-$C_6$)-alkyl, ($C_2$-$C_6$)-alkenyl, ($C_2$-$C_6$)-alkynyl, ($C_3$-$C_6$)-cycloalkyl or ($C_3$-$C_6$)-cycloalkyl-($C_1$-$C_6$)-alkyl, $R^4$ is ($C_1$-$C_6$)-alkyl, ($C_2$-$C_6$)-alkenyl or ($C_2$-$C_6$)-alkynyl, $R^5$ is methyl or ethyl, $R^6$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, ($C_1$-$C_6$)-alkoxy, ($C_3$-$C_6$)-cycloalkyl, or heteroaryl, heterocyclyl or phenyl each substituted by s radicals from the group of methyl, ethyl, methoxy, trifluoromethyl and halogen, n is 0, 1 or 2, s is 0, 1, 2 or 3, $M^+$ is a cation selected from the group consisting of sodium ion, potassium ion, lithium ion, magnesium ion, calcium ion, $NH_4^+$ ion, (2-hydroxyeth-1-yl)ammonium ion, bis-N,N-(2-hydroxyeth-1-yl)-ammonium ion, tris-N,N,N-(2-hydroxyeth-1-yl)ammonium ion, tetra-N,N,N,N-(2-hydroxyeth-1-yl)ammonium ion, N-(2-hydroxyeth-1-yl)-tris-N,N,N-methylammonium ion, methylammonium ion, dimethylammonium ion, trimethylammonium ion, tetramethylammonium ion, ethylammonium ion, diethylammonium ion, triethylammonium ion, tetraethylammonium ion, isopropylammonium ion, diisopropylammonium ion, tetrapropylammonium ion, tetrabutylammonium ion, tetraoctylammonium ion, 2-(2-hydroxyeth-1-oxy)eth-1-ylammonium ion, di-(2-hydroxyeth-1-yl)ammonium ion, trimethylbenzylammonium ion, triethylbenzylammonium ion, tri-(($C_1$-$C_4$)-alkyl)sulfonium ion, benzylammonium ion, 1-phenylethylammonium ion, 2-phenylethylammonium ion, diisopropylethylammonium ion, pyridinium ion, piperidinium ion, imidazolium ion, morpholinium ion, 1,8-diazabicyclo[5.4.0]undec-7-enium ion.

In the formula (I) and all the formulae which follow, alkyl radicals having more than two carbon atoms may be straight-chain or branched. Alkyl radicals are, for example, methyl, ethyl, n-propyl or isopropyl, n-, iso-, t- or 2-butyl, pentyls, hexyls such as n-hexyl, isohexyl and 1,3-dimethylbutyl. Analogously, alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-yn-1-yl, 1-methylbut-3-yn-1-yl. The multiple bond may be in any position in each unsaturated radical. Cycloalkyl is a carbocyclic saturated ring system having three to six carbon atoms, for example cyclopropyl, cyclobutyl, cyclopentyl or cyclohexyl. Analogously, cycloalkenyl is a monocyclic alkenyl group having three to six carbon ring members, for example cyclopropenyl, cyclobutenyl, cyclopentenyl and cyclohexenyl, where the double bond may be in any position.

Halogen is fluorine, chlorine, bromine or iodine.

Heterocyclyl is a saturated, partly saturated or fully unsaturated cyclic radical which contains 3 to 6 ring atoms, of which 1 to 4 are from the group of oxygen, nitrogen and sulfur, and which may additionally be fused by a benzo ring. For example, heterocyclyl is piperidinyl, pyrrolidinyl, tetrahydrofuranyl, dihydrofuranyl and oxetanyl.

Heteroaryl is an aromatic cyclic radical which contains 3 to 6 ring atoms, of which 1 to 4 are from the group of oxygen, nitrogen and sulfur, and which may additionally be fused by a benzo ring. For example, heteroaryl is benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

If a group is polysubstituted by radicals, this should be understood to mean that this group is substituted by one or more identical or different radicals selected from the radicals mentioned. The same applies to the formation of ring systems by different atoms and elements.

The definition of the cation $M^+$ should be understood such that the inventive salts of the formula (I) are in uncharged form. In the case of monovalent cations, this means that an anion is present as counterion. In the case of polyvalent cations, for example di- or trivalent cations, two or three anions are present as counterions.

Preference is given to inventive compounds of the formula (I) in which

A is N or CY,

R is hydrogen, ($C_1$-$C_6$)-alkyl, ($C_3$-$C_7$)-cycloalkyl, halo-($C_1$-$C_6$)-alkyl, ($C_3$-$C_7$)-cycloalkylmethyl, methoxycarbonylmethyl, ethoxycarbonylmethyl, acetylmethyl, methoxymethyl, methoxyethyl, benzyl, pyrazin-2-yl, furan-2-yl, tetrahydrofuran-2-yl, morpholine, dimethylamino, or phenyl substituted by s radicals from the group of methyl, methoxy, trifluoromethyl and halogen;

X is nitro, halogen, cyano, ($C_1$-$C_6$)-alkyl, halo-($C_1$-$C_6$)-alkyl, ($C_3$-$C_6$)-cycloalkyl, $OR^1$, $S(O)_nR^2$, ($C_1$-$C_6$)-alkyl-$S(O)_nR^2$, ($C_1$-$C_6$)-alkyl-$OR^1$, ($C_1$-$C_6$)-alkyl-$CON(R^1)_2$, ($C_1$-$C_6$)-alkyl-$SO_2N(R^1)_2$, ($C_1$-$C_6$)-alkyl-$NR^1COR^1$, ($C_1$-$C_6$)-alkyl-$NR^1SO_2R^2$, ($C_1$-$C_6$)-alkylheteroaryl, ($C_1$-$C_6$)-alkylheterocyclyl, where the two latter radicals are each substituted by s halogen, ($C_1$-$C_6$)-alkyl, halo-($C_1$-$C_6$)-alkyl, $S(O)_n$—($C_1$-$C_6$)-alkyl, ($C_1$-$C_6$)-alkoxy, halo-($C_1$-$C_6$)-alkoxy radicals, and where heterocyclyl bears n oxo groups, Y is hydrogen, nitro, halogen, cyano, ($C_1$-$C_6$)-alkyl, ($C_1$-$C_6$)-haloalkyl, $OR^1$, $S(O)_nR^2$, $SO_2N(R^1)_2$, $N(R^1)_2$, $NR^1SO_2R^2$, $NR^1COR^1$, ($C_1$-$C_6$)-alkyl-$S(O)_nR^2$, ($C_1$-$C_6$)-alkyl-$OR^1$, ($C_1$-$C_6$)-alkyl-$CON(R^1)_2$, ($C_1$-$C_6$)-alkyl-$SO_2N(R^1)_2$, ($C_1$-$C_6$)-alkyl-$NR^1COR^1$, ($C_1$-$C_6$)-alkyl-$NR^1SO_2R^2$, ($C_1$-$C_6$)-alkylphenyl, ($C_1$-$C_6$)-alkylheteroaryl, ($C_1$-$C_6$)-alkylheterocyclyl, phenyl, heteroaryl or heterocyclyl, where the 6 latter radicals are each substituted by s radicals from the group of halogen, nitro, cyano, ($C_1$-$C_6$)-alkyl, halo-($C_1$-$C_6$)-alkyl, ($C_3$-$C_6$)-cycloalkyl, $S(O)_n$—($C_1$-$C_6$)-alkyl, ($C_1$-$C_6$)-alkoxy, halo-($C_1$-$C_6$)-alkoxy, ($C_1$-$C_6$)-alkoxy-($C_1$-$C_4$)-alkyl and cyanomethyl, and where heterocyclyl bears n oxo groups, Z is halogen, cyano, nitro, methyl, halo-($C_1$-$C_6$)-alkyl, ($C_3$-$C_6$)-cycloalkyl, $S(O)_nR^2$, 1,2,4-triazol-1-yl, pyrazol-1-yl, or Z may also be hydrogen if Y is the $S(O)_nR^2$ radical, $R^1$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where the 16 latter radicals are substituted by s radicals from the group consisting of cyano, halogen, nitro, $OR^3$, $S(O)_nR^4$, $N(R^3)_2$, $NR^3OR^3$, $COR^3$, $OCOR^3$, $NR^3COR^3$, $NR^3SO_2R^4$, $CO_2R^3$, $CON(R^3)_2$ and $(C_1-C_4)$-alkoxy-$(C_2-C_6)$-alkoxycarbonyl, and where heterocyclyl bears n oxo groups, $R^2$ is $(C_1-C_6)$-alkyl, $(C_3-C_6)$-cycloalkyl or $(C_3-C_6)$-cycloalkyl-$(C_1-C_6)$-alkyl, where these three aforementioned radicals are each substituted by s radicals from the group consisting of halogen and $OR^3$, $R^3$ is hydrogen or $(C_1-C_6)$-alkyl, $R^4$ is $(C_1-C_6)$-alkyl, n is 0, 1 or 2, s is 0, 1, 2 or 3, M+ is a cation selected from the group consisting of sodium ion, potassium ion, lithium ion, magnesium ion, calcium ion, $NH_4$ ion, (2-hydroxyeth-1-yl)ammonium ion, bis-N,N-(2-hydroxyeth-1-yl)-ammonium ion, tris-N,N,N-(2-hydroxyeth-1-yl)ammonium ion, tetra-N,N,N,N-(2-hydroxyeth-1-yl)ammonium ion, N-(2-hydroxyeth-1-yl)-tris-N,N,N-methylammonium ion, methylammonium ion, dimethylammonium ion, trimethylammonium ion, tetramethylammonium ion, ethylammonium ion, diethylammonium ion, triethylammonium ion, tetraethylammonium ion, isopropylammonium ion, diisopropylammonium ion, tetrapropylammonium ion, tetrabutylammonium ion, tetraoctylammonium ion, 2-(2-hydroxyeth-1-oxy)eth-1-ylammonium ion, di-(2-hydroxyeth-1-yl)ammonium ion, trimethylbenzylammonium ion, triethylbenzylammonium ion, tri-((C1-C4)-alkyl)sulfonium ion, benzylammonium ion, 1-phenylethylammonium ion, 2-phenylethylammonium ion, diisopropylethylammonium ion, pyridinium ion, piperidinium ion, imidazolium ion, morpholinium ion, 1,8-diazabicyclo[5.4.0]undec-7-enium ion.

Particular preference is given to inventive compounds of the formula (I) in which A is N or CY, R is $C_1-C_6$)-alkyl, $(C_3-C_7)$-cycloalkyl or methoxymethyl, X is halogen, $(C_1-C_6)$-alkyl, halo-$(C_1-C_6)$-alkyl, $OR^1$ or $S(O)_nR^2$, Y is $(C_1-C_6)$-alkyl, $(C_1-C_6)$-haloalkyl, $OR^1$ or $S(O)_nR^2$, Z is halogen, methyl, halo-$(C_1-C_6)$-alkyl or $S(O)_nR^2$, $R^1$ is hydrogen, $(C_1-C_6)$-alkyl or $(C_3-C_6)$-cycloalkyl, $R^2$ is $(C_1-C_6)$-alkyl, n is 0, 1 or 2, s is 0, 1, 2 or 3, M+ is a cation selected from the group consisting of sodium ion, potassium ion, lithium ion, magnesium ion, calcium ion and $NH_4^+$ ion.

Compounds of the invention can be prepared, for example, by the method shown in scheme 1, by deprotonation of an N-(1,3,4-oxadiazol-2-yl)benzamide and -nicotinamide (II) with a suitable base of the formula $M^+B^-$ (scheme 1), where $B^-$, for example, hydride, hydroxyl or alkoxy anions, such as methoxy, ethoxy, n-propoxy, i-propoxy, n-butoxy or t-butoxy.

Schema 1

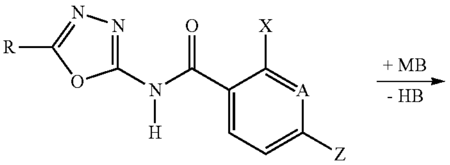

(II)

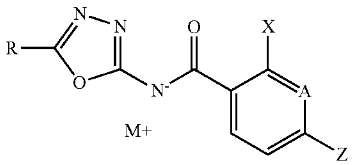

(I)

The compounds of the formula (II) are known from WO 2012/126932 A1 and can be obtained by the methods described therein.

The inventive compounds of the formula (I) have excellent herbicidal activity against a broad spectrum of economically important mono- and dicotyledonous annual harmful plants. The active ingredients also have good control over perennial harmful plants which are difficult to control and produce shoots from rhizomes, root stocks or other perennial organs.

The present invention therefore also provides a method for controlling unwanted plants or for regulating the growth of plants, preferably in plant crops, in which one or more compound(s) of the invention is/are applied to the plants (for example harmful plants such as monocotyledonous or dicotyledonous weeds or unwanted crop plants), the seed (for example grains, seeds or vegetative propagules such as tubers or shoot parts with buds) or the area on which the plants grow (for example the area under cultivation). The compounds of the invention can be deployed, for example, prior to sowing (if appropriate also by incorporation into the soil), prior to emergence or after emergence. Specific examples of some representatives of the monocotyledonous and dicotyledonous weed flora which can be controlled by the compounds of the invention are as follows, though the enumeration is not intended to impose a restriction to particular species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria* and *Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphe-*

*noclea, Stellaria, Taraxacum, Thlaspi, Trifolium, Urtica, Veronica, Viola* and *Xanthium*.

If the compounds of the invention are applied to the soil surface before germination, either the emergence of the weed seedlings is prevented completely or the weeds grow until they have reached the cotyledon stage, but then they stop growing and ultimately die completely after three to four weeks have passed.

If the active ingredients are applied post-emergence to the green parts of the plants, growth stops after the treatment, and the harmful plants remain at the growth stage of the point of time of application, or they die completely after a certain time, so that in this manner competition by the weeds, which is harmful to the crop plants, is eliminated very early and in a sustained manner.

Although the compounds of the invention have outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*, will be damaged to a negligible extent only, if at all, depending on the structure of the particular compound of the invention and its application rate. For these reasons, the present compounds are very suitable for selective control of unwanted plant growth in plant crops such as agriculturally useful plants or ornamental plants.

In addition, the compounds of the invention (depending on their particular structure and the application rate deployed) have outstanding growth-regulating properties in crop plants. They intervene in the plants' own metabolism with regulatory effect, and can thus be used for the controlled influencing of plant constituents and to facilitate harvesting, for example by triggering desiccation and stunted growth. Furthermore, they are also suitable for the general control and inhibition of unwanted vegetative growth without killing the plants in the process. Inhibition of vegetative growth plays a major role for many mono- and dicotyledonous crops since, for example, this can reduce or completely prevent lodging.

By virtue of their herbicidal and plant growth regulatory properties, the active ingredients can also be used to control harmful plants in crops of genetically modified plants or plants modified by conventional mutagenesis. In general, the transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or those with a different fatty acid composition in the harvested material.

It is preferable, with respect to transgenic crops, to use the compounds of the invention in economically important transgenic crops of useful plants and ornamentals, for example of cereals such as wheat, barley, rye, oats, millet/*sorghum*, rice and corn or else crops of sugar beet, cotton, soybean, oilseed rape, potato, tomato, peas and other types of vegetable. It is preferred to employ the compounds of the invention as herbicides in crops of useful plants which are resistant, or have been made resistant by recombinant means, to the phytotoxic effects of the herbicides.

It is preferred to use the compounds of the invention in economically important transgenic crops of useful plants and ornamentals, for example of cereals such as wheat, barley, rye, oats, millet/*sorghum*, rice, cassava and corn or else crops of sugar beet, cotton, soybean, oilseed rape, potato, tomato, peas and other vegetables. Preferably, the compounds of the invention can be used as herbicides in crops of useful plants which are resistant, or have been made resistant by genetic engineering, to the phytotoxic effects of the herbicides.

Conventional ways of producing novel plants which have modified properties in comparison to existing plants consist, for example, in traditional cultivation methods and the generation of mutants. Alternatively, novel plants with modified properties can be generated with the aid of recombinant methods (see, for example, EP-A-0221044, EP-A-0131624). For example, there have been descriptions in several cases of:

- genetic modifications of crop plants for the purpose of modifying the starch synthesized in the plants (e.g. WO 92/11376, WO 92/14827, WO 91/19806),
- transgenic crop plants which are resistant to particular herbicides of the glufosinate type (cf., for example, EP-A-0242236, EP-A-242246) or glyphosate type (WO 92/00377) or the sulfonylurea type (EP-A-0257993, U.S. Pat. No. 5,013,659),
- transgenic crop plants, for example cotton, capable of producing *Bacillus thuringiensis* toxins (Bt toxins), which make the plants resistant to particular pests (EP-A-0142924, EP-A-0193259),
- transgenic crop plants with a modified fatty acid composition (WO 91/13972),
- genetically modified crop plants with novel constituents or secondary metabolites, for example novel phytoalexins, which bring about an increased disease resistance (EPA 309862, EPA0464461),
- genetically modified plants having reduced photorespiration, which have higher yields and higher stress tolerance (EPA 0305398),
- transgenic crop plants which produce pharmaceutically or diagnostically important proteins ("molecular pharming"),
- transgenic crop plants which feature higher yields or better quality,
- transgenic crop plants which feature a combinations, for example, of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431).

For such recombinant manipulations, nucleic acid molecules which allow mutagenesis or sequence alteration by recombination of DNA sequences can be introduced into plasmids. With the aid of standard methods, it is possible, for example, to undertake base exchanges, remove parts of sequences or add natural or synthetic sequences. For the connection of the DNA fragments to one another, adapters or linkers may be added to the fragments; see, for example, Sambrook et al., 1989, Molecular Cloning, A Laboratory Manual, 2nd ed. Cold Spring Harbor Laboratory Press, Cold Spring Harbor, N.Y., or Winnacker "Gene und Klone", VCH Weinheim 2nd edition 1996

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Sequences of this kind are known to those skilled in the art (see, for example, Braun et al., EMBO J. 11 (1992), 3219-3227, Wolter et al., Proc. Natl. Acad. Sci. USA 85 (1988), 846-850, Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences.

The compounds of the invention can be used with preference in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients.

When the active ingredients of the invention are employed in transgenic crops, not only do the effects toward harmful plants observed in other crops occur, but frequently also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the compounds of the invention as herbicides for control of harmful plants in transgenic crop plants.

Compared to their corresponding acids, the compounds of the invention have higher solubility in water and therefore, for example, more advantageous formulation properties. They are highly suitable for preparing water-based formulations.

The compounds of the invention can be applied in the form of wettable powders, emulsifiable concentrates, sprayable solutions, dusting products or granules in the customary formulations. The invention therefore also provides herbicidal and plant-growth-regulating compositions which comprise the compounds of the invention.

The compounds of the invention can be formulated in various ways, according to the biological and/or physicochemical parameters required. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes. These individual formulation types are known in principle and are described, for example, in: Winnacker-Küchler, "Chemische Technologie", volume 7, C. Hanser Verlag München, 4th ed. 1986, Wade van Valkenburg, "Pesticide Formulations", Marcel Dekker, N.Y., 1973, K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry", 2nd Ed., J. Wiley & Sons, N.Y., C. Marsden, "Solvents Guide", 2nd Ed., Interscience, N.Y. 1963, McCutcheon's "Detergents and Emulsifiers Annual", MC Publ. Corp., Ridgewood N.J., Sisley and Wood, "Encyclopedia of Surface Active Agents", Chem. Publ. Co. Inc., N.Y. 1964, Schönfeldt, "Grenzflächenaktive Äthylenoxidaddukte", Wiss. Verlagsgesell, Stuttgart 1976, Winnacker-Küchler, "Chemische Technologie", volume 7, C. Hanser Verlag München, 4th ed. 1986.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tankmix. Suitable safeners are, for example, mefenpyr-diethyl, cyprosulfamide, isoxadifen-ethyl, cloquintocet-mexyl and dichlormid.

Wettable powders are preparations which can be dispersed uniformly in water and, in addition to the active ingredient, apart from a diluent or inert substance, also comprise surfactants of the ionic and/or nonionic type (wetting agents, dispersants), for example polyethoxylated alkylphenols, polyethoxylated fatty alcohols, polyethoxylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the active herbicidal ingredients are finely ground, for example in customary apparatuses such as hammer mills, blower mills and air-jet mills, and simultaneously or subsequently mixed with the formulation auxiliaries.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active ingredient with finely distributed solids, for example talc, natural clays, such as kaolin, bentonite and pyrophillite, or diatomaceous earth.

Suspension concentrates may be water- or oil-based. They may be prepared, for example, by wet-grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be produced either by spraying the active ingredient onto adsorptive granular inert material or by applying active ingredient concentrates to the surface of carriers, such as sand, kaolinites or granular inert material, by means of adhesives, for example polyvinyl alcohol, sodium polyacrylate or else mineral oils. Suitable active ingredients can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London, J. E. Browning, "Agglomeration", Chemical and Engineering 1967, pages 147 ff, "Perry's Chemical Engineer's Handbook", 5th Ed., McGraw-Hill, New York 1973, S. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations contain generally 0.1 to 99% by weight, especially 0.1 to 95% by weight, of compounds of the invention.

In wettable powders, the active ingredient concentration is, for example, about 10% to 90% by weight, the remainder to 100% by weight consisting of customary formulation constituents. In emulsifiable concentrates, the active ingredient concentration may be about 1% to 90% and preferably 5% to 80% by weight. Dust-type formulations contain 1% to 30% by weight of active ingredient, preferably usually 5% to 20% by weight of active ingredient; sprayable solutions contain about 0.05% to 80% by weight, preferably 2% to 50% by weight of active ingredient. In the case of water-dispersible granules, the active ingredient content depends partially on whether the active ingredient is in liquid or solid form and on which granulation auxiliaries, fillers, etc., are used. In the water-dispersible granules, the content of active ingredient is, for example, between 1% and 95% by weight, preferably between 10% and 80% by weight.

In addition, the active ingredient formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tankmix.

For application, the formulations in commercial form are, if appropriate, diluted in a customary manner, for example in the case of wettable powders, emulsifiable concentrates, dispersions and water-dispersible granules with water. Dust-type preparations, granules for soil application or granules for scattering and sprayable solutions are not normally diluted further with other inert substances prior to application.

The required application rate of the compounds of the formula (I) varies with the external conditions, including temperature, humidity and the type of herbicide used. It can vary within wide limits, for example between 0.001 and 1.0 kg/ha or more of active substance, but it is preferably between 0.005 and 750 g/ha.

The examples below illustrate the invention.

A. CHEMICAL EXAMPLES

Preparation of the sodium salt of 2-methyl-N-(5-methyl-1,3,4-oxadiazol-2-yl)-3-(methylsulfonyl)-4-(trifluoromethyl)benzamide (No. 1-14)

To a solution of 200 mg (0.55 mmol) of 2-methyl-N-(5-methyl-1,3,4-oxadiazol-2-yl)-3-(methylsulfonyl)-4-(trifluoromethyl)benzamide in 5 ml of methanol was added, at room temperature (RT), 0.101 ml (0.55 mmol) of a 30% sodium methoxide solution in methanol. After stirring at RT for 8 h, the mixture was concentrated. The residue was twice admixed with 5 ml of abs. toluene and concentrated to dryness.

Yield: 0.21 g (0.55 mmol; 99%).

$^1$H-NMR (DMSO-$d_6$, 400 MHz): 7.79 (d, 1H), 7.67 (d, 1H), 3.34 (s; 3H); 2.71 (s, 3H), 2.28 (s, 3H).

Preparation of the beta-hydroxyethyltrimethylammonium Salt of 2-chloro-N-(5-methyl-1,3,4-oxadiazol-2-yl)-3-(methylsulfinyl)-4-(trifluoromethyl) benzamide (No. 1-153)

To a solution of 100 mg (0.272 mmol) of 2-chloro-N-(5-methyl-1,3,4-oxadiazol-2-yl)-3-(methylsulfinyl)-4-(trifluoromethyl)benzamide in 2.5 ml of methanol was added, at RT, a solution of 0.077 ml (0.272 mmol) of a 45% solution of beta-hydroxyethyltrimethylammonium hydroxide. After stirring at RT for 8 h, the mixture was concentrated. The residue was twice admixed with 5 ml of toluene and concentrated to dryness.

Yield: 0.12 g (0.25 mmol; 94%).

$^1$H-NMR (DMSO-$d_6$, 400 MHz): 7.74 (d, 1H), 7.65 (d, 1H), 4.06 (bs, 2H); 3.72 (bs, 2H); 3.28 (s, 9H); 3.11 (s, 3H); 2.38 (s, 3H).

The examples listed in the tables below were prepared analogously to the abovementioned methods or are obtainable analogously to the abovementioned methods. The compounds listed in the tables below are very particularly preferred.

Very especially preferred are salts of N-(1,3,4-oxadiazol-2-yl)benzamides of formula (I) in which A is CY, R is methyl, X is methyl, Y methylsulfonyl, Z trifluoromethyl, M+ is a cation selected from the group consisting of sodium ion, potassium ion, NH4+ ion, N-(2-hydroxyeth-1-yl)-tris-N,N,N-methylammonium ion, tetramethylammonium ion, tetrapropylammonium ion, tetraoctylammonium ion, trimethylbenzylammonium ion.

The abbreviations used here are:

| | | |
|---|---|---|
| Ac = acetyl | Bn = benzyl | Bu = n-butyl |
| c-Pr = c-propyl | Et = ethyl | Me = methyl |
| n-Oct = n-octyl | Pr = n-propyl | |

TABLE 1

Compounds of the general formula (I) in which A is CY

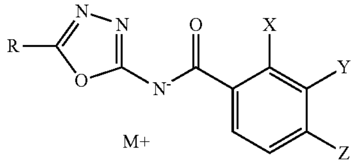

| No. | R | X | Y | Z | $M^+$ | Physical data ($^1$H NMR, DMSO-$d_6$, 400 MHz) |
|---|---|---|---|---|---|---|
| 1-1 | Me | Cl | H | $SO_2Me$ | $Na^+$ | |
| 1-2 | Me | $SO_2Me$ | H | $CF_3$ | $Na^+$ | |
| 1-3 | Me | $SO_2Me$ | H | $CF_3$ | $Pr_4N^+$ | |
| 1-4 | Me | $SO_2Me$ | H | $CF_3$ | $Me_3N(CH_2CH_2OH)^+$ | |
| 1-5 | Me | SMe | SMe | $CF_3$ | $Na^+$ | |
| 1-6 | Me | SMe | SOMe | $CF_3$ | $Na^+$ | |
| 1-7 | Me | SMe | $SO_2Me$ | $CF_3$ | $Na^+$ | |
| 1-8 | Me | Me | SMe | $CF_3$ | $Na^+$ | |
| 1-9 | Me | Me | SMe | $C_2F_5$ | $Na^+$ | |
| 1-10 | c-Pr | Me | SMe | $CF_3$ | $Na^+$ | |
| 1-11 | Me | Me | SOMe | $CF_3$ | $Na^+$ | |
| 1-12 | Me | Me | SOMe | $CF_3$ | $Me_3N(CH_2CH_2OH)^+$ | |
| 1-13 | Et | Me | SOMe | $CF_3$ | $Na^+$ | |
| 1-14 | Me | Me | $SO_2Me$ | $CF_3$ | $Na^+$ | 7.79 (d, 1H), 7.67 (d, 1H), 3.34 (s; 3H); 2.71 (s, 3H), 2.28 (s, 3H) |
| 1-15 | Me | Me | $SO_2Me$ | $CF_3$ | $Li^+$ | 7.83 (d, 1H), 7.74 (d, 1H), 3.34 (s; 3H); 2.72 (s, 3H), 2.33 (s, 3H) |
| 1-16 | Me | Me | $SO_2Me$ | $CF_3$ | $K^+$ | 7.78 (d, 1H), 7.66 (d, 1H), 3.36 (s; 3H); 2.71 (s, 3H), 2.28 (s, 3H) |
| 1-17 | Me | Me | $SO_2Me$ | $CF_3$ | $Mg^{2+}$ | |
| 1-18 | Me | Me | $SO_2Me$ | $CF_3$ | $Ca^{2+}$ | |
| 1-19 | Me | Me | $SO_2Me$ | $CF_3$ | $Me_3S^+$ | |
| 1-20 | Me | Me | $SO_2Me$ | $CF_3$ | $Et_3S^+$ | |
| 1-21 | Me | Me | $SO_2Me$ | $CF_3$ | $Me_4N^+$ | 7.77 (d, 1H), 7.63 (d, 1H), 3.33 (s; 3H); 3.10 (s, 12H), 2.70 (s, 3H), 2.27 (s, 3H) |
| 1-22 | Me | Me | $SO_2Me$ | $CF_3$ | $Et_4N^+$ | 7.81 (d, 1H), 7.69 (d, 1H), 3.34 (s; 3H); 3.20 (q, 8H), 2.70 (s, 3H), 2.30 (s, 3H), 1.15 (t, 12H) |
| 1-23 | Me | Me | $SO_2Me$ | $CF_3$ | $Bu_4N^+$ | |
| 1-24 | Me | Me | $SO_2Me$ | $CF_3$ | $i\text{-}Pr_4N^+$ | |
| 1-25 | Me | Me | $SO_2Me$ | $CF_3$ | $Et_3N(Bn)^+$ | 7.67 (d, 1H), 7.61 (d, 1H), 7.49-7.38 (m, 5H); 4.57 (s, 2H); 3.30 (q, 6H), 3.18 (s, 3H); 2.84 (s, 3H); 2.38 (s, 3H); 1.41 (t, 9H) |

TABLE 1-continued

Compounds of the general formula (I) in which A is CY

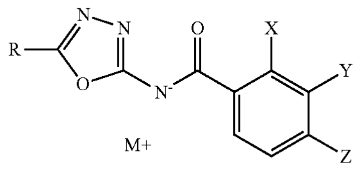

| No. | R | X | Y | Z | $M^+$ | Physical data ($^1H$ NMR, DMSO-$d_6$, 400 MHz) |
|---|---|---|---|---|---|---|
| 1-26 | Me | Me | $SO_2Me$ | $CF_3$ | $Pr_4N^+$ | 7.77 (d, 1H), 7.70 (d, 1H), 3.24-3.19 (m, 11H); 2.90 (s, 3H); 2.39 (s, 3H); 1.71-1.65 (m, 8H); 0.96 (t, 12H) |
| 1-27 | Me | Me | $SO_2Me$ | $CF_3$ | $Me_3N(CH_2CH_2OH)^+$ | 7.73 (2d, 2H), 4.00 (bs, 2H); 3.64-3.62 (m, 2H); 3.27 (s, 9H); 3.20 (s, 3H), 2.82 (s, 3H); 2.38 (s, 3H);) |
| 1-28 | Me | Me | $SO_2Me$ | $CF_3$ | $Me_3N(Bn)^+$ | 7.71 (2d, 2H), 7.50-7.45 (m, 5H); 4.71 (s, 2H); 3.24 (s,9H), 3.20 (s, 3H); 2.79 (s, 3H); 2.43 (s, 3H) |
| 1-29 | Me | Me | $SO_2Me$ | $CF_3$ | n-$Oct_4N^+$ | 7.76 (d, 1H), 7.69 (d, 1H), 3.27-3.22 (m, 8H); 3.18 (s, 3H); 2.37 (s, 3H); 1.62 (m, 8H); 1.30-1.25 (m, 40H); 0.88 (t, 12H) |
| 1-30 | Me | Me | SOMe | $C_2F_5$ | $Na^+$ | |
| 1-31 | $MeOCH_2$ | Me | $SO_2Me$ | $CF_3$ | $Na^+$ | |
| 1-32 | $MeOCH_2$ | Me | $SO_2Me$ | $CF_3$ | $Me_3N(CH_2CH_2OH)^+$ | |
| 1-33 | Pr | Me | $SO_2Me$ | $CF_3$ | $Na^+$ | |
| 1-34 | $MeO(CH_2)_2$— | Me | $SO_2Me$ | $CF_3$ | $Na^+$ | |
| 1-35 | Me | Me | SEt | $CF_3$ | $Na^+$ | |
| 1-36 | Et | Me | SEt | $CF_3$ | $Na^+$ | |
| 1-37 | Me | Me | SOEt | $CF_3$ | $Na^+$ | |
| 1-38 | Me | Me | SOEt | $CHF_2$ | $Na^+$ | |
| 1-39 | Me | Me | $SO_2Et$ | $CF_3$ | $Na^+$ | |
| 1-40 | Et | Me | $SO_2Et$ | $CF_3$ | $Na^+$ | |
| 1-41 | Me | Me | $SO_2Et$ | $CHF_2$ | $Na^+$ | |
| 1-42 | Me | Me | 1H-pyrazol-1-yl | $CF_3$ | $Na^+$ | |
| 1-43 | Me | Me | 1H-pyrazol-1-yl | $CF_3$ | $Me_3N(CH_2CH_2OH)^+$ | |
| 1-44 | Me | Me | 1H-pyrazol-1-yl | $C_2F_5$ | $Na^+$ | |
| 1-45 | Me | Me | 4-$CF_3$-1H-pyrazol-1-yl | $CF_3$ | $Na^+$ | |
| 1-46 | Me | Me | 4-Me-1H-pyrazol-1-yl | $CF_3$ | $Na^+$ | |
| 1-47 | Me | Me | 2H-1,2,3-triazol-2-yl | $CF_3$ | $Na^+$ | |
| 1-48 | Me | Me | 2H-1,2,3-triazol-2-yl | $C_2F_5$ | $Na^+$ | |
| 1-49 | Me | Me | 1H-1,2,3-triazol-1-yl | $CF_3$ | $Na^+$ | |
| 1-50 | Me | Me | 1H-1,2,3-triazol-1-yl | $CF_3$ | $Na^+$ | |
| 1-51 | Me | Me | 1H-1,2,4-triazol-1-yl | $CF_3$ | $Na^+$ | |
| 1-52 | Me | Me | 1H-1,2,4-triazol-1-yl | $C_2F_5$ | $Na^+$ | |
| 1-53 | Me | Me | SMe | CN | $Na^+$ | |
| 1-54 | Me | Me | SOMe | CN | $Na^+$ | |
| 1-55 | Me | Me | $SO_2Me$ | CN | $Na^+$ | |
| 1-56 | Me | Me | SMe | Cl | $Na^+$ | |
| 1-57 | Me | Me | SOMe | Cl | $Na^+$ | |
| 1-58 | Me | Me | $SO_2Me$ | Cl | $Na^+$ | |
| 1-59 | Me | Me | SEt | Cl | $Na^+$ | |
| 1-60 | Me | Me | SOEt | Cl | $Na^+$ | |
| 1-61 | Et | Me | SOEt | Cl | $Na^+$ | |
| 1-62 | Me | Me | $SO_2Et$ | Cl | $Na^+$ | |
| 1-63 | Me | Me | SMe | Br | $Na^+$ | |
| 1-64 | Me | Me | SEt | Br | $Na^+$ | |

TABLE 1-continued

Compounds of the general formula (I) in which A is CY

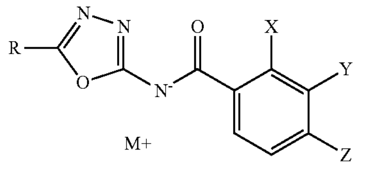

| No. | R | X | Y | Z | $M^+$ | Physical data ($^1H$ NMR, DMSO-$d_6$, 400 MHz) |
|---|---|---|---|---|---|---|
| 1-65 | Me | Me | Ac | $SO_2Me$ | $Na^+$ | |
| 1-66 | Me | Me | (CO)-c-Pr | $SO_2Me$ | $Na^+$ | |
| 1-67 | Me | Me | C(=NOMe)Me | $SO_2Me$ | $Na^+$ | |
| 1-68 | Me | Me | C(=NOEt)Me | $SO_2Me$ | $Na^+$ | |
| 1-69 | Me | Me | 5-c-Pr-isoxazol-3-yl | $SO_2Me$ | $Na^+$ | |
| 1-70 | Me | Me | 5-methoxymethyl-1,2-oxazol-3-yl | $SO_2Me$ | $Na^+$ | |
| 1-71 | Me | Me | 3-methyl-4,5-dihydro-1,2-oxazol-5-yl | $SO_2Me$ | $Na^+$ | |
| 1-72 | Me | Me | 4,5-dihydro-1,2-oxazol-3-yl | $SO_2Me$ | $Na^+$ | |
| 1-73 | Et | Me | 4,5-dihydro-1,2-oxazol-3-yl | $SO_2Me$ | $Na^+$ | |
| 1-74 | Me | Me | pyrazol-1-yl | $SO_2Me$ | $Na^+$ | |
| 1-75 | $MeOCH_2$ | Me | pyrazol-1-yl | $SO_2Me$ | $Na^+$ | |
| 1-76 | Me | Me | 4-$CF_3$-1H-pyrazol-1-yl | $SO_2Me$ | $Na^+$ | |
| 1-77 | Me | Me | 4-Cl-1H-pyrazol-yl | $SO_2Me$ | $Na^+$ | 8.29 (s, 1H), 7.92 (s, 1H), 7.90 (d, 1H), 7.82 (d, 1H), 3.09 (s, 3H), 2.50 (s, 3H), 2.30 (s, 3H) |
| 1-78 | Me | Me | OMe | $SO_2Me$ | $Na^+$ | |
| 1-79 | Me | Me | SMe | $SO_2Me$ | $Na^+$ | |
| 1-80 | Me | Me | SOMe | $SO_2Me$ | $Na^+$ | |
| 1-81 | Me | Me | $SO_2Me$ | $SO_2Me$ | $Na^+$ | |
| 1-82 | Et | Me | $SO_2Me$ | $SO_2Me$ | $Na^+$ | |
| 1-83 | Me | Me | SEt | $SO_2Me$ | $Na^+$ | |
| 1-84 | Me | Me | SOEt | $SO_2Me$ | $Na^+$ | |
| 1-85 | Me | Me | $SO_2Et$ | $SO_2Me$ | $Na^+$ | |
| 1-86 | Me | Me | $SO_2Et$ | $SO_2Et$ | $Na^+$ | |
| 1-87 | Et | Me | $SO_2Et$ | $SO_2Me$ | $Na^+$ | |
| 1-88 | Me | Me | $SCH_2CH_2OMe$ | $SO_2Me$ | $Na^+$ | |
| 1-89 | Me | Me | $SOCH_2CH_2OMe$ | $SO_2Me$ | $Na^+$ | |
| 1-90 | Me | Me | $SO_2CH_2CH_2OMe$ | $SO_2Me$ | $Na^+$ | |
| 1-91 | Me | Et | SMe | $CF_3$ | $Na^+$ | |
| 1-92 | Me | Et | SOMe | $CF_3$ | $Na^+$ | |
| 1-93 | Me | Et | $SO_2Me$ | $CF_3$ | $Na^+$ | |
| 1-94 | Me | Et | SEt | $CF_3$ | $Na^+$ | |
| 1-95 | Me | Et | SOEt | $CF_3$ | $Na^+$ | |
| 1-96 | Me | Et | $SO_2Et$ | $CF_3$ | $Na^+$ | |
| 1-97 | Me | Et | SMe | Cl | $Na^+$ | |
| 1-98 | Et | Et | SMe | Cl | $Na^+$ | |
| 1-99 | Me | Et | SOMe | Cl | $Na^+$ | |
| 1-100 | Me | Et | SEt | Cl | $Na^+$ | |
| 1-101 | Me | Et | SOEt | Cl | $Na^+$ | |
| 1-102 | Me | Et | $SO_2Et$ | Cl | $Na^+$ | |
| 1-103 | Me | Et | SMe | Br | $Na^+$ | |
| 1-104 | Me | Et | $SO_2Me$ | Br | $Na^+$ | |
| 1-105 | Me | Pr | SMe | $CF_3$ | $Na^+$ | |
| 1-106 | Me | Pr | SOMe | $CF_3$ | $Na^+$ | |
| 1-107 | Me | c-Pr | SMe | $CF_3$ | $Na^+$ | |
| 1-108 | Me | c-Pr | SOMe | $CF_3$ | $Na^+$ | |
| 1-109 | Me | c-Pr | $SO_2Me$ | $CF_3$ | $Na^+$ | |
| 1-110 | Me | $CH_2OMe$ | SMe | $CF_3$ | $Na^+$ | |
| 1-111 | Me | $CH_2OMe$ | SOMe | $CF_3$ | $Na^+$ | |
| 1-112 | Me | $CH_2OMe$ | $SO_2Me$ | $CF_3$ | $Na^+$ | |
| 1-113 | Me | $CH_2OMe$ | SEt | $CF_3$ | $Na^+$ | |
| 1-114 | Me | $CH_2OMe$ | SOEt | $CF_3$ | $Na^+$ | |
| 1-115 | Me | $CH_2OMe$ | $SO_2Et$ | $CF_3$ | $Na^+$ | |
| 1-116 | Me | $CH_2OMe$ | SMe | $SO_2Me$ | $Na^+$ | |
| 1-117 | Me | $CH_2OMe$ | SOMe | $SO_2Me$ | $Na^+$ | |

TABLE 1-continued

Compounds of the general formula (I) in which A is CY

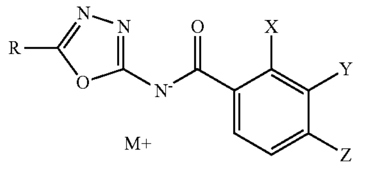

| No. | R | X | Y | Z | $M^+$ | Physical data ($^1H$ NMR, DMSO-$d_6$, 400 MHz) |
|---|---|---|---|---|---|---|
| 1-118 | Me | $CH_2OMe$ | $SO_2Me$ | $SO_2Me$ | $Na^+$ | |
| 1-119 | Me | OMe | SMe | $CF_3$ | $Na^+$ | |
| 1-120 | Me | OMe | SMe | $CF_3$ | $Me_3N(CH_2CH_2OH)^+$ | |
| 1-121 | Me | OMe | SOMe | $CF_3$ | $Na^+$ | |
| 1-122 | Me | OMe | SOMe | $CF_3$ | $Me_3N(CH_2CH_2OH)^+$ | |
| 1-123 | Me | OMe | $SO_2Me$ | $CF_3$ | $Na^+$ | |
| 1-124 | Me | OMe | $SO_2Me$ | $CF_3$ | $Me_3N(CH_2CH_2OH)^+$ | |
| 1-125 | Me | OMe | SMe | $CHF_2$ | $Na^+$ | |
| 1-126 | Me | OMe | SMe | $CHF_2$ | $Pr_4N^+$ | |
| 1-127 | Me | OMe | SMe | $CHF_2$ | $Me_3N(CH_2CH_2OH)^+$ | |
| 1-128 | Et | OMe | SMe | $CHF_2$ | $Na^+$ | |
| 1-129 | Et | OMe | SMe | $CHF_2$ | $Pr_4N^+$ | |
| 1-130 | Et | OMe | SMe | $CHF_2$ | $Me_3N(CH_2CH_2OH)^+$ | |
| 1-131 | Me | OMe | SOMe | $CHF_2$ | $Na^+$ | |
| 1-132 | Me | OMe | SOMe | $CHF_2$ | $Pr_4N^+$ | |
| 1-133 | Me | OMe | SOMe | $CHF_2$ | $Me_3N(CH_2CH_2OH)^+$ | |
| 1-134 | Et | OMe | SOMe | $CHF_2$ | $Na^+$ | |
| 1-135 | Et | OMe | SOMe | $CHF_2$ | $Pr_4N^+$ | |
| 1-136 | Et | OMe | SOMe | $CHF_2$ | $Me_3N(CH_2CH_2OH)^+$ | |
| 1-137 | Me | OMe | $SO_2Me$ | $CHF_2$ | $Na^+$ | |
| 1-138 | Me | OMe | $SO_2Me$ | $CHF_2$ | $Pr_4N^+$ | |
| 1-139 | Me | OMe | $SO_2Me$ | $CHF_2$ | $Me_3N(CH_2CH_2OH)^+$ | |
| 1-140 | Et | OMe | $SO_2Me$ | $CHF_2$ | $Na^+$ | |
| 1-141 | Et | OMe | $SO_2Me$ | $CHF_2$ | $Pr_4N^+$ | |
| 1-142 | Et | OMe | $SO_2Me$ | $CHF_2$ | $Me_3N(CH_2CH_2OH)^+$ | |
| 1-143 | Me | OMe | SEt | $CF_3$ | $Na^+$ | |
| 1-144 | Me | OMe | SOEt | $CF_3$ | $Na^+$ | |
| 1-145 | Me | OMe | $SO_2Et$ | $CF_3$ | $Na^+$ | |
| 1-146 | Me | Cl | SMe | H | $Na^+$ | |
| 1-147 | Me | Cl | $SO_2Me$ | Me | $Na^+$ | |
| 1-148 | Me | Cl | $SO_2Et$ | Me | $Na^+$ | |
| 1-149 | Me | Cl | SMe | $CF_3$ | $Na^+$ | |
| 1-150 | Me | Cl | SOMe | $CF_3$ | $Na^+$ | 7.80 (d, 1H), 7.64 (d, 1H), 3.10 (s, 3H), 2.28 (s, 3H) |
| 1-151 | Me | Cl | SOMe | $CF_3$ | $Et_3N(Bn)^+$ | 7.68 (d, 1H), 7.53 (d, 1H), 7.47-7.41 (m, 5H); 4.65 (s, 2H);+ 3.35 (q, 6H), 3.09 (s, 3H); 2.38 (s, 3H); 1.43 (t, 9H) |
| 1-152 | Me | Cl | SOMe | Cl | $Pr_4N^+$ | 7.75 (d, 1H), 7.63 (d, 1H), 3.27-3.23 (m, 8H); 3.10 (s, 3H); 2.39 (s, 3H); 1.73-1.67 (m, 8H); 0.95 (t, 12H) |
| 1-153 | Me | Cl | SOMe | Cl | $Me_3N(CH_2CH_2OH)^+$ | B7.74 (d, 1H), 7.65 (d, 1H), 4.06 (bs, 2H); 3.72 (bs, 2H); 3.28 (s, 9H); 3.11 (s, 3H); 2.38 (s, 3H) |
| 1-154 | Me | Cl | SOMe | Cl | $Me_3N(Bn)^+$ | 7.74 (d, 1H), 6.65 d, 1H), 7.50-7.45 (m, 5H);4.73 (s, 2H); 3.26 (s,9H), 3.10 (s, 3H); 2.41 (s, 3H) |
| 1-155 | Me | Cl | SOMe | Cl | $n\text{-}Oct_4N^+$ | 7.75 (d, 1H), 7.62 (d, 1H), 3.29-3.25 (m, 8H); 3.09 (s, 3H); 2.37 (s, 3H); 1.64 (m, 8H); 1.28-1.24 (m, 48H); 0.87 (t, 12H) |
| 1-156 | Me | Cl | SOMe | $CF_3$ | $Et_3N(Bn)^+$ | 7.68 (d, 1H), 7.53 (d, 1H), 7.47-7.41 (m, |

TABLE 1-continued

Compounds of the general formula (I) in which A is CY

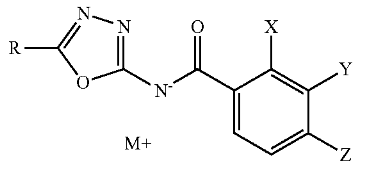

| No. | R | X | Y | Z | $M^+$ | Physical data ($^1H$ NMR, DMSO-$d_6$, 400 MHz) |
|---|---|---|---|---|---|---|
| | | | | | | 5H); 4.65 (s, 2H); 3.35 (q, 6H), 3.09 (s, 3H); 2.38 (s, 3H); 1.43 (t, 9H) |
| 1-157 | Me | Cl | SOMe | $CF_3$ | $Li^+$ | 7.84 (d, 1H), 7.71 (d, 1H), 3.11 (s, 3H), 2.33 (s, 3H) |
| 1-158 | Me | Cl | SOMe | $CF_3$ | $K^+$ | 7.82 (d, 1H), 7.68 (d, 1H), 3.10 (s, 3H), 2.30 (s, 3H) |
| 1-159 | Me | Cl | SOMe | $CF_3$ | $Mg^{2+}$ | |
| 1-160 | Me | Cl | SOMe | $CF_3$ | $Ca^{2+}$ | |
| 1-161 | Me | Cl | SOMe | $CF_3$ | $Me_3S^+$ | |
| 1-162 | Me | Cl | SOMe | $CF_3$ | $Et_3S^+$ | |
| 1-163 | Me | Cl | SOMe | $CF_3$ | $Me_4N^+$ | 7.78 (d, 1H), 7.61 (d, 1H), 3.10 (s, 12H), 3.09 (s, 3H), 2.26 (s, 3H) |
| 1-164 | Me | Cl | SOMe | $CF_3$ | $Et_4N^+$ | 7.83 (d, 1H), 7.69 (d, 1H), 3.20 (q, 8H), 3.10 (s, 3H), 1.15 (t, 12H) |
| 1-165 | Me | Cl | SOMe | $CF_3$ | $Bu_4N^+$ | |
| 1-166 | Me | Cl | SOMe | $CF_3$ | $i\text{-}Pr_4N^+$ | |
| 1-167 | Me | Cl | $SO_2Me$ | $CF_3$ | $Na^+$ | 7.94 (d, 1H), 7.76 (d, 1H), 3.49 (s, 3H), 2.28 (s, 3H) |
| 1-168 | Me | Cl | $SO_2Me$ | $CF_3$ | $Me_3N(CH_2CH_2OH)^+$ | |
| 1-169 | Me | Cl | $SO_2Me$ | $CF_3$ | $Et_4N^+$ | 7.91 (d, 1H), 7.73 (d, 1H), 3.47 (s, 3H), 3.19 (q, 8H), 2.28 (s, 3H), 1.16 (t, 12H). |
| 1-170 | c-Pr | Cl | $SO_2Me$ | $CF_3$ | $Na^+$ | 7.93 (d, 1H), 7.75 (d, 1H), 3.50 (s, 3H), 2.00-1.96 (m, 1H), 0.99-0.94 (m, 2H), 0.84-0.80 (m, 2H) |
| 1-171 | c-Pr | Cl | $SO_2Me$ | $CF_3$ | $Pr_4N^+$ | |
| 1-172 | Me | Cl | $SO_2Me$ | c-Pr | $Na^+$ | |
| 1-173 | Me | Cl | $SO_2Et$ | $CF_3$ | $Na^+$ | |
| 1-174 | Me | Cl | SOEt | c-Pr | $Na^+$ | 7.41 (d, 1H), 6.92 (d, 1H), 3.41-3.19 (m, 2H), 2.28 (s, 3H), 1.24 3H), 0.64-0.57 (m, 1H) |
| 1-175 | Me | Cl | $SO_2Et$ | c-Pr | $Na^+$ | |
| 1-176 | Me | Cl | $SCH_2$-c-Pr | c-Pr | $Na^+$ | |
| 1-177 | Me | Cl | $SOCH_2$-c-Pr | c-Pr | $Na^+$ | |
| 1-178 | Me | Cl | $SO_2CH_2$-c-Pr | c-Pr | $Na^+$ | |
| 1-179 | Me | Cl | $S(CH_2)_2OMe$ | c-Pr | $Na^+$ | |
| 1-180 | Me | Cl | $SO(CH_2)_2OMe$ | c-Pr | $Na^+$ | |
| 1-181 | Me | Cl | $SO_2(CH_2)_2OMe$ | c-Pr | $Na^+$ | |
| 1-182 | Me | Cl | 1H-pyrazol-1-yl | $CF_3$ | $Na^+$ | 7.96 (d, 1H), 7.82 (d, 1H), 7.75 (d, 1H), 7.74 (d, 1H), 6.51 (dd, 1H), 3.32 (s, 3H), 2.28 (s, 3H) |
| 1-183 | Me | Cl | 1H-pyrazol-1-yl | $CF_3$ | $Me_3N(CH_2CH_2OH)^+$ | |
| 1-184 | Me | Cl | 1H-pyrazol-1-yl | $C_2F_5$ | $Na^+$ | |
| 1-185 | Me | Cl | 4-$CF_3$-1H-pyrazol-1-yl | $CF_3$ | $Na^+$ | |
| 1-186 | Me | Cl | 4-Me-1H-pyrazol-1-yl | $CF_3$ | $Na^+$ | |
| 1-187 | Me | Cl | 2H-1,2,3-triazol-2-yl | $CF_3$ | $Na^+$ | |

TABLE 1-continued

Compounds of the general formula (I) in which A is CY

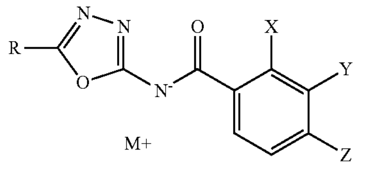

| No. | R | X | Y | Z | $M^+$ | Physical data ($^1$H NMR, DMSO-$d_6$, 400 MHz) |
|---|---|---|---|---|---|---|
| 1-188 | Me | Cl | 2H-1,2,3-triazol-2-yl | $C_2F_5$ | $Na^+$ | |
| 1-189 | Me | Cl | 1H-1,2,3-triazol-1-yl | $CF_3$ | $Na^+$ | |
| 1-190 | Me | Cl | 1H-1,2,3-triazol-1-yl | $C_2F_5$ | $Na^+$ | |
| 1-191 | Me | Cl | 1H-1,2,4-triazol-1-yl | $CF_3$ | $Na^+$ | |
| 1-192 | Me | Cl | 1H-1,2,4-triazol-1-yl | $C_2F_5$ | $Na^+$ | |
| 1-193 | Me | Cl | 1H-pyrazol-1-yl | $SO_2Me$ | $Na^+$ | |
| 1-194 | Me | Cl | 1H-pyrazol-1-yl | $SO_2Me$ | $Me_3N(CH_2CH_2OH)^+$ | |
| 1-195 | Me | Cl | 2-Br-1H-pyrazol-1-yl | $SO_2Me$ | $Na^+$ | |
| 1-196 | Me | Cl | 4-$CF_3$-1H-pyrazol-1-yl | $SO_2Me$ | $Na^+$ | |
| 1-197 | Me | Cl | 4-Me-1H-pyrazol-1-yl | $SO_2Me$ | $Na^+$ | |
| 1-198 | Me | Cl | 2H-1,2,3-triazol-2-yl | $SO_2Me$ | $Na^+$ | |
| 1-199 | Me | Cl | 1H-1,2,4-triazol-1-yl | $SO_2Me$ | $Na^+$ | |
| 1-200 | Me | Cl | 1H-1,2,3-triazol-1-yl | $SO_2Me$ | $Na^+$ | |
| 1-201 | Me | Cl | $OCH_2CH_2OMe$ | Cl | $Na^+$ | |
| 1-202 | Me | Cl | SMe | Cl | $Na^+$ | |
| 1-203 | Et | Cl | SMe | Cl | $Na^+$ | |
| 1-204 | Me | Cl | SOMe | Cl | $Na^+$ | |
| 1-205 | Et | Cl | SOMe | Cl | $Na^+$ | |
| 1-206 | Me | Cl | $SO_2Me$ | Cl | $Na^+$ | |
| 1-207 | Et | Cl | $SO_2Me$ | Cl | $Na^+$ | |
| 1-208 | Me | Cl | SEt | Cl | $Na^+$ | |
| 1-209 | Me | Cl | SOEt | Cl | $Na^+$ | |
| 1-210 | Me | Cl | $SO_2Et$ | Cl | $Na^+$ | |
| 1-211 | Me | Cl | $SCH_2CH_2OMe$ | $SO_2Me$ | $Na^+$ | |
| 1-212 | Me | Cl | $SOCH_2CH_2OMe$ | $SO_2Me$ | $Na^+$ | |
| 1-213 | Me | Cl | $SO_2CH_2CH_2OMe$ | $SO_2Me$ | $Na^+$ | |
| 1-214 | Me | Cl | $CH_2OMe$ | $SO_2Me$ | $Na^+$ | |
| 1-215 | Me | Cl | $CH_2OMe$ | $SO_2Me$ | $K^+$ | |
| 1-216 | Me | Cl | $CH_2OMe$ | $SO_2Me$ | $Pr_4N^+$ | |
| 1-217 | Me | Cl | $CH_2OMe$ | $SO_2Me$ | $Me_3N(CH_2CH_2OH)^+$ | |
| 1-218 | Me | Cl | $CH_2OCH_2CF_3$ | $SO_2Me$ | $Na^+$ | |
| 1-219 | Et | Cl | $CH_2OCH_2CF_3$ | $SO_2Me$ | $Na^+$ | |
| 1-220 | Me | Cl | $CH_2OCH_2CH_2OMe$ | $SO_2Me$ | $Na^+$ | |
| 1-221 | Me | Cl | Ac | $SO_2Me$ | $Na^+$ | |
| 1-222 | Me | Cl | (CO)-c-Pr | $SO_2Me$ | $Na^+$ | |
| 1-223 | Me | Cl | C(=NOMe)Me | $SO_2Me$ | $Na^+$ | |
| 1-224 | Me | Cl | C(=NOEt)Me | $SO_2Me$ | $Na^+$ | |
| 1-225 | Me | Cl | 5-c-Pr-isoxazol-3-yl | $SO_2Me$ | $Na^+$ | |
| 1-226 | Me | Cl | 5-methoxymethyl-1,2-oxazol-3-yl | $SO_2Me$ | $Na^+$ | |
| 1-227 | Me | Cl | 3-methyl-4,5-dihydro-1,2-oxazol-5-yl | $SO_2Me$ | $Na^+$ | |
| 1-228 | Me | Cl | 4,5-dihydro-1,2-oxazol-3-yl | $SO_2Me$ | $Na^+$ | |
| 1-229 | Me | Cl | 2H-1,2,3-triazol-2-yl | $SO_2Me$ | $Na^+$ | |
| 1-230 | Me | Cl | 2H-1,2,3-triazol-2-yl | $SO_2Me$ | $Me_3N(CH_2CH_2OH)^+$ | |
| 1-231 | Me | Cl | 4,5-dihydro-1,2-oxazol-3-yl | $SO_2Et$ | $Na^+$ | |

TABLE 1-continued

Compounds of the general formula (I) in which A is CY

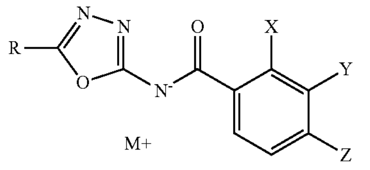

| No. | R | X | Y | Z | $M^+$ | Physical data ($^1H$ NMR, DMSO-$d_6$, 400 MHz) |
|---|---|---|---|---|---|---|
| 1-232 | Me | Cl | 5-cyanomethyl-4,5-dihydro-1,2-oxazol-3-yl | $SO_2Et$ | $Na^+$ | |
| 1-233 | Me | Cl | 5-cyanomethyl-4,5-dihydro-1,2-oxazol-3-yl | $SO_2Et$ | $Pr_4N^+$ | |
| 1-234 | Me | Cl | 5-cyanomethyl-4,5-dihydro-1,2-oxazol-3-yl | $SO_2Et$ | $Me_3N(CH_2CH_2OH)^+$ | |
| 1-235 | Me | Cl | 5-cyanomethyl-4,5-dihydro-1,2-oxazol-3-yl | $SO_2Et$ | $Li^+$ | |
| 1-236 | Me | Cl | 5-cyanomethyl-4,5-dihydro-1,2-oxazol-3-yl | $SO_2Et$ | $K^+$ | |
| 1-237 | Me | Cl | 5-cyanomethyl-4,5-dihydro-1,2-oxazol-3-yl | $SO_2Et$ | $Mg^{2+}$ | |
| 1-238 | Me | Cl | 5-cyanomethyl-4,5-dihydro-1,2-oxazol-3-yl | $SO_2Et$ | $Ca^{2+}$ | |
| 1-239 | Me | Cl | 5-cyanomethyl-4,5-dihydro-1,2-oxazol-3-yl | $SO_2Et$ | $Me_3S^+$ | |
| 1-240 | Me | Cl | 5-cyanomethyl-4,5-dihydro-1,2-oxazol-3-yl | $SO_2Et$ | $Et_3S^+$ | |
| 1-241 | Me | Cl | 5-cyanomethyl-4,5-dihydro-1,2-oxazol-3-yl | $SO_2Et$ | $Me_4N^+$ | |
| 1-242 | Me | Cl | 5-cyanomethyl-4,5-dihydro-1,2-oxazol-3-yl | $SO_2Et$ | $Et_4N^+$ | |
| 1-243 | Et | Cl | 5-methoxymethyl-4,5-dihydro-1,2-oxazol-3 yl | $SO_2Et$ | $Na^+$ | 7.88 (d, 1H), 7.71 (d, 1H), 5.02-4.89 (m, 1H), 3.60-3.31 (m, 9H); 3.11-3.01 (m, 1H); 1.18 (t, 3H), 1.09 (t, 3H) |
| 1-244 | Et | Cl | 5-methoxymethyl-4,5-dihydro-1,2-oxazol-3 yl | $SO_2Et$ | $Et_4N^+$ | 7.86 (d, 1H), 7.67 (d, 1H), 5.01-4.89 (m, 1H), 3.59-3.23 (m, 9H); 3.22-3.17 (m, 8H), 3.11-3.01 (m, 1H); 1.20- 1.09 (m, 18H) |
| 1-245 | Me | Cl | OMe | $SO_2Me$ | $Na^+$ | |
| 1-246 | Me | Cl | OMe | $SO_2Et$ | | |
| 1-247 | Me | Cl | OEt | $SO_2Me$ | $Na^+$ | 7.75 (d, 1H), 7.40 (d, 1H), 4.19 (q, 2H), 3.32 (s, 3H), 2.32 (s, 3H), 1.41 (t, 3H) |
| 1-248 | Me | Cl | OEt | $SO_2Et$ | $Na^+$ | |
| 1-249 | Me | Cl | OPr | $SO_2Me$ | $Na^+$ | |
| 1-250 | Me | Cl | OPr | $SO_2Et$ | $Na^+$ | |
| 1-251 | Me | Cl | O-$CHF_2$ | $SO_2Me$ | $Na^+$ | |
| 1-252 | Me | Cl | o-propargyl | $SO_2Me$ | $Na^+$ | |
| 1-253 | Me | Cl | $OCH_2$c-Pr | $SO_2Me$ | $Na^+$ | |
| 1-254 | Me | Cl | $OCH_2$c-Pr | $SO_2Et$ | $Na^+$ | 7.68 (d, 1H), 7.35 (d, 1H), 3.98-3.91 (m, 2H), 3.51-3.44 (m, 2H), 2.28 (s, 3H), 1.38 - 1.35 (m, 1H), |

TABLE 1-continued

Compounds of the general formula (I) in which A is CY

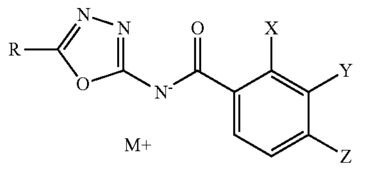

| No. | R | X | Y | Z | $M^+$ | Physical data ($^1H$ NMR, DMSO-$d_6$, 400 MHz) |
|---|---|---|---|---|---|---|
| | | | | | | 1.10 (t, 3H), 0.63-0.59 (m, 2H), 0.43-0.39 (m, 2H) |
| 1-255 | Me | Cl | $O(CH_2)_2Cl$ | $SO_2Me$ | $Na^+$ | |
| 1-256 | Me | Cl | $O(CH_2)_2F$ | $SO_2Me$ | $Na^+$ | |
| 1-257 | Me | Cl | $OCH_2CF_3$ | $SO_2Et$ | $Na^+$ | |
| 1-258 | Me | Cl | $O(CH_2)3OMe$ | $SO_2Me$ | $Na^+$ | 7.70 (d, 1H), 7.35 (d, 1H), 4.19 (t, 2H), 3.54 (t, 2H), 3.27 (s, 3H), 2.28 (s, 3H), 2.10-2.05 (m, 2H) |
| 1-259 | Me | Cl | $OCH_2$-1,3-dioxolan-2-yl | $SO_2Me$ | $Na^+$ | |
| 1-260 | Me | Cl | SMe | $SO_2Me$ | $Na^+$ | |
| 1-261 | Me | Cl | SOMe | $SO_2Me$ | $Na^+$ | |
| 1-262 | Me | Cl | $SO_2Me$ | $SO_2Me$ | $Na^+$ | |
| 1-263 | Me | Cl | SEt | $SO_2Me$ | $Na^+$ | |
| 1-264 | Me | Cl | SOEt | $SO_2Me$ | $Na^+$ | |
| 1-265 | Me | Cl | $SO_2Et$ | $SO_2Me$ | $Na^+$ | |
| 1-266 | Me | Cl | $SCH_2CH_2OMe$ | $SO_2Me$ | $Na^+$ | |
| 1-267 | Me | Cl | $SOCH_2CH_2OMe$ | $SO_2Me$ | $Na^+$ | |
| 1-268 | Me | Cl | $SO_2CH_2CH_2OMe$ | $SO_2Me$ | $Na^+$ | |
| 1-269 | Me | Br | 1H-pyrazol-1-yl | $CF_3$ | $Na^+$ | |
| 1-270 | Me | Br | 1H-pyrazol-1-yl | $C_2F_5$ | $Na^+$ | |
| 1-271 | Me | Br | 2H-1,2,3-triazol-2-yl | $CF_3$ | $Na^+$ | |
| 1-272 | Me | Br | 2H-1,2,3-triazol-2-yl | $C_2F_5$ | $Na^+$ | |
| 1-273 | Me | Br | 1H-1,2,3-triazol-1-yl | CF3 | $Na^+$ | |
| 1-274 | Me | Br | 1H-1,2,3-triazol-1-yl | $C_2F_5$ | $Na^+$ | |
| 1-275 | Me | Br | 1H-1,2,4-triazol-1-yl | $CF_3$ | $Na^+$ | |
| 1-276 | Me | Br | 1H-1,2,4-triazol-1-yl | $C_2F_5$ | $Na^+$ | |
| 1-277 | Me | Me | SMe | Me | $Na^+$ | |
| 1-278 | Me | Me | SOMe | Me | $Na^+$ | |
| 1-279 | Me | Me | $SO_2Me$ | Me | $Na^+$ | |
| 1-280 | Me | Me | SEt | Me | $Na^+$ | |
| 1-281 | Me | Me | SOEt | Me | $Na^+$ | |
| 1-282 | Me | Me | $SO_2Et$ | Me | $Na^+$ | |
| 1-283 | Me | Me | S-c-Pr | Me | $Na^+$ | |
| 1-284 | Me | Me | SO-c-Pr | Me | $Na^+$ | |
| 1-285 | Me | Me | $SO_2$-c-Pr | Me | $Na^+$ | |
| 1-286 | Me | Me | $SCH_2$-c-Pr | Me | $Na^+$ | |
| 1-287 | Me | Me | $SOCH_2$-c-Pr | Me | $Na^+$ | |
| 1-288 | Me | Me | $SO_2CH_2$c-Pr | Me | $Na^+$ | |
| 1-289 | Me | Me | $SCH_2CH_2OMe$ | Me | $Na^+$ | |
| 1-290 | Me | Me | $SOCH_2CH_2OMe$ | Me | $Na^+$ | |
| 1-291 | Me | Me | $SO_2CH_2CH_2OMe$ | Me | $Na^+$ | |
| 1-292 | Me | Me | SMe | Et | $Na^+$ | |
| 1-293 | Me | Me | SOMe | Et | $Na^+$ | |
| 1-294 | Me | Me | $SO_2Me$ | Et | $Na^+$ | |
| 1-295 | Me | Me | SEt | Et | $Na^+$ | |
| 1-296 | Me | Me | SOEt | Et | $Na^+$ | |
| 1-297 | Me | Me | $SO_2Et$ | Et | $Na^+$ | |
| 1-298 | Me | Me | S-c-Pr | Et | $Na^+$ | |
| 1-299 | Me | Me | SO-c-Pr | Et | $Na^+$ | |
| 1-300 | Me | Me | $SO_2$-c-Pr | Et | $Na^+$ | |
| 1-301 | Me | Me | $SCH_2$-c-Pr | Et | $Na^+$ | |
| 1-302 | Me | Me | $SOCH_2$-c-Pr | Et | $Na^+$ | |
| 1-303 | Me | Me | $SO_2CH_2$-c-Pr | Et | $Na^+$ | |
| 1-304 | Me | Me | $SCH_2CH_2OMe$ | Et | $Na^+$ | |
| 1-305 | Me | Me | $SOCH_2CH_2OMe$ | Et | $Na^+$ | |

TABLE 1-continued

Compounds of the general formula (I) in which A is CY

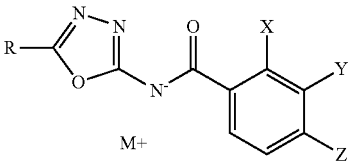

| No. | R | X | Y | Z | $M^+$ | Physical data ($^1H$ NMR, DMSO-$d_6$, 400 MHz) |
|---|---|---|---|---|---|---|
| 1-306 | Me | Me | $SO_2CH_2CH_2OMe$ | Et | $Na^+$ | |
| 1-307 | Me | Me | SMe | i-Pr | $Na^+$ | |
| 1-308 | Me | Me | SOMe | i-Pr | $Na^+$ | |
| 1-309 | Me | Me | $SO_2Me$ | i-Pr | $Na^+$ | |
| 1-310 | Me | Me | SEt | i-Pr | $Na^+$ | |
| 1-311 | Me | Me | SOEt | i-Pr | $Na^+$ | |
| 1-312 | Me | Me | $SO_2Et$ | i-Pr | $Na^+$ | |
| 1-313 | Me | Me | S-c-Pr | i-Pr | $Na^+$ | |
| 1-314 | Me | Me | SO-c-Pr | i-Pr | $Na^+$ | |
| 1-315 | Me | Me | $SO_2$-c-Pr | i-Pr | $Na^+$ | |
| 1-316 | Me | Me | $SCH_2$-c-Pr | i-Pr | $Na^+$ | |
| 1-317 | Me | Me | $SOCH_2$-c-Pr | i-Pr | $Na^+$ | |
| 1-318 | Me | Me | $SO_2CH_2$-c-Pr | i-Pr | $Na^+$ | |
| 1-319 | Me | Me | $SCH_2CH_2OMe$ | i-Pr | $Na^+$ | |
| 1-320 | Me | Me | $SOCH_2CH_2OMe$ | i-Pr | $Na^+$ | |
| 1-321 | Me | Me | $SO_2CH_2CH_2OMe$ | i-Pr | $Na^+$ | |
| | Me | | | | | |
| | Me | | | | | |
| | Me | | | | | |
| 1-322 | Me | Et | SMe | Me | $Na^+$ | |
| 1-323 | Me | Et | SOMe | Me | $Na^+$ | |
| 1-324 | Me | Et | $SO_2Me$ | Me | $Na^+$ | |
| 1-325 | Me | Et | SEt | Me | $Na^+$ | |
| 1-326 | Me | Et | SOEt | Me | $Na^+$ | |
| 1-327 | Me | Et | $SO_2Et$ | Me | $Na^+$ | |
| 1-328 | Me | Et | S-c-Pr | Me | $Na^+$ | |
| 1-329 | Me | Et | SO-c-Pr | Me | $Na^+$ | |
| 1-330 | Me | Et | $SO_2$-c-Pr | Me | $Na^+$ | |
| 1-331 | Me | Et | $SCH_2$-c-Pr | Me | $Na^+$ | |
| 1-332 | Me | Et | $SOCH_2$c-Pr | Me | $Na^+$ | |
| 1-333 | Me | Et | $SO_2CH_2$-c-Pr | Me | $Na^+$ | |
| 1-334 | Me | Et | $SCH_2CH_2OMe$ | Me | $Na^+$ | |
| 1-335 | Me | Et | $SOCH_2CH_2OMe$ | Me | $Na^+$ | |
| 1-336 | Me | Et | $SO_2CH_2CH_2OMe$ | Me | $Na^+$ | |
| 1-337 | Me | Et | SMe | Et | $Na^+$ | |
| 1-338 | Me | Et | SOMe | Et | $Na^+$ | |
| 1-339 | Me | Et | $SO_2Me$ | Et | $Na^+$ | |
| 1-340 | Me | Et | SEt | Et | $Na^+$ | |
| 1-341 | Me | Et | SOEt | Et | $Na^+$ | |
| 1-342 | Me | Et | $SO_2Et$ | Et | $Na^+$ | |
| 1-343 | Me | Et | S-c-Pr | Et | $Na^+$ | |
| 1-344 | Me | Et | SO-c-Pr | Et | $Na^+$ | |
| 1-345 | Me | Et | $SO_2$-c-Pr | Et | $Na^+$ | |
| 1-346 | Me | Et | $SCH_2$-c-Pr | Et | $Na^+$ | |
| 1-347 | Me | Et | $SOCH_2$-c-Pr | Et | $Na^+$ | |
| 1-348 | Me | Et | $SO_2CH_2$c-Pr | Et | $Na^+$ | |
| 1-349 | Me | Et | $SCH_2CH_2OMe$ | Et | $Na^+$ | |
| 1-350 | Me | Et | $SOCH_2CH_2OMe$ | Et | $Na^+$ | |
| 1-351 | Me | Et | $SO_2CH_2CH_2OMe$ | Et | $Na^+$ | |
| 1-352 | Me | Et | SMe | i-Pr | $Na^+$ | |
| 1-353 | Me | Et | SOMe | i-Pr | $Na^+$ | |
| 1-354 | Me | Et | $SO_2Me$ | i-Pr | $Na^+$ | |
| 1-355 | Me | Et | SEt | i-Pr | $Na^+$ | |
| 1-356 | Me | Et | SOEt | i-Pr | $Na^+$ | |
| 1-357 | Me | Et | $SO_2Et$ | i-Pr | $Na^+$ | |
| 1-358 | Me | Et | S-c-Pr | i-Pr | $Na^+$ | |
| 1-359 | Me | Et | SO-c-Pr | i-Pr | $Na^+$ | |
| 1-360 | Me | Et | $SO_2$-c-Pr | i-Pr | $Na^+$ | |
| 1-361 | Me | Et | $SCH_2$-c-Pr | i-Pr | $Na^+$ | |
| 1-362 | Me | Et | $SOCH_2$-c-Pr | i-Pr | $Na^+$ | |
| 1-363 | Me | Et | $SO_2CH_2$-c-Pr | i-Pr | $Na^+$ | |
| 1-364 | Me | Et | $SCH_2CH_2OMe$ | i-Pr | $Na^+$ | |
| 1-365 | Me | Et | $SOCH_2CH_2OMe$ | i-Pr | $Na^+$ | |
| 1-366 | Me | Et | $SO_2CH_2CH_2OMe$ | i-Pr | $Na^+$ | |
| 1-367 | Me | c-Pr | SMe | Me | $Na^+$ | |

TABLE 1-continued

Compounds of the general formula (I) in which A is CY

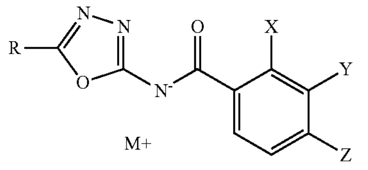

| No. | R | X | Y | Z | $M^+$ | Physical data ($^1H$ NMR, DMSO-$d_6$, 400 MHz) |
|---|---|---|---|---|---|---|
| 1-368 | Me | c-Pr | SOMe | Me | $Na^+$ | |
| 1-369 | Me | c-Pr | $SO_2Me$ | Me | $Na^+$ | |
| 1-370 | Me | c-Pr | SEt | Me | $Na^+$ | |
| 1-371 | Me | c-Pr | SOEt | Me | $Na^+$ | |
| 1-372 | Me | c-Pr | $SO_2Et$ | Me | $Na^+$ | |
| 1-373 | Me | c-Pr | S-c-Pr | Me | $Na^+$ | |
| 1-374 | Me | c-Pr | SO-c-Pr | Me | $Na^+$ | |
| 1-375 | Me | c-Pr | $SO_2$-c-Pr | Me | $Na^+$ | |
| 1-376 | Me | c-Pr | $SCH_2$-c-Pr | Me | $Na^+$ | |
| 1-377 | Me | c-Pr | $SOCH_2$-c-Pr | Me | $Na^+$ | |
| 1-378 | Me | c-Pr | $SO_2CH_2$-c-Pr | Me | $Na^+$ | |
| 1-379 | Me | c-Pr | $SCH_2CH_2OMe$ | Me | $Na^+$ | |
| 1-380 | Me | c-Pr | $SOCH_2CH_2OMe$ | Me | $Na^+$ | |
| 1-381 | Me | c-Pr | $SO_2CH_2CH_2OMe$ | Me | $Na^+$ | |
| 1-382 | Me | c-Pr | SMe | Et | $Na^+$ | |
| 1-383 | Me | c-Pr | SOMe | Et | $Na^+$ | |
| 1-384 | Me | c-Pr | $SO_2Me$ | Et | $Na^+$ | |
| 1-385 | Me | c-Pr | SEt | Et | $Na^+$ | |
| 1-386 | Me | c-Pr | SOEt | Et | $Na^+$ | |
| 1-387 | Me | c-Pr | $SO_2Et$ | Et | $Na^+$ | |
| 1-388 | Me | c-Pr | S-c-Pr | Et | $Na^+$ | |
| 1-389 | Me | c-Pr | SO-c-Pr | Et | $Na^+$ | |
| 1-390 | Me | c-Pr | $SO_2$-c-Pr | Et | $Na^+$ | |
| 1-391 | Me | c-Pr | $SCH_2$-c-Pr | Et | $Na^+$ | |
| 1-392 | Me | c-Pr | $SOCH_2$-c-Pr | Et | $Na^+$ | |
| 1-393 | Me | c-Pr | $SO_2CH_2$-c-Pr | Et | $Na^+$ | |
| 1-394 | Me | c-Pr | $SCH_2CH_2OMe$ | Et | $Na^+$ | |
| 1-395 | Me | c-Pr | $SOCH_2CH_2OMe$ | Et | $Na^+$ | |
| 1-396 | Me | c-Pr | $SO_2CH_2CH_2OMe$ | Et | $Na^+$ | |
| 1-397 | Me | c-Pr | SMe | i-Pr | $Na^+$ | |
| 1-398 | Me | c-Pr | SOMe | i-Pr | $Na^+$ | |
| 1-399 | Me | c-Pr | $SO_2Me$ | i-Pr | $Na^+$ | |
| 1-400 | Me | c-Pr | SEt | i-Pr | $Na^+$ | |
| 1-401 | Me | c-Pr | SOEt | i-Pr | $Na^+$ | |
| 1-402 | Me | c-Pr | $SO_2Et$ | i-Pr | $Na^+$ | |
| 1-403 | Me | c-Pr | S-c-Pr | i-Pr | $Na^+$ | |
| 1-404 | Me | c-Pr | SO-c-Pr | i-Pr | $Na^+$ | |
| 1-405 | Me | c-Pr | $SO_2$-c-Pr | i-Pr | $Na^+$ | |
| 1-406 | Me | c-Pr | $SCH_2$-c-Pr | i-Pr | $Na^+$ | |
| 1-407 | Me | c-Pr | $SOCH_2$-c-Pr | i-Pr | $Na^+$ | |
| 1-408 | Me | c-Pr | $SO_2CH_2$-c-Pr | i-Pr | $Na^+$ | |
| 1-409 | Me | c-Pr | $SCH_2CH_2OMe$ | i-Pr | $Na^+$ | |
| 1-410 | Me | c-Pr | $SOCH_2CH_2OMe$ | i-Pr | $Na^+$ | |
| 1-411 | Me | c-Pr | $SO_2CH_2CH_2OMe$ | i-Pr | $Na^+$ | |

TABLE 2

Compounds of the general formula (I) in which A is N

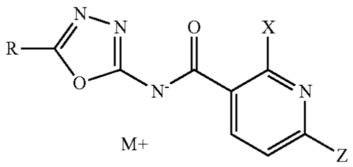

| No. | R | X | Z | $M^+$ | Physical data ($^1H$ NMR, DMSO-$d_6$, 400 MHz) |
|---|---|---|---|---|---|
| 2-1 | Me | Me | $CF_3$ | $Na^+$ | 8.16 (d, 1H), 7.68 (d, 1H), 3.18 (s, 3H), 2.33 (s, 3H) |

TABLE 2-continued

Compounds of the general formula (I) in which A is N

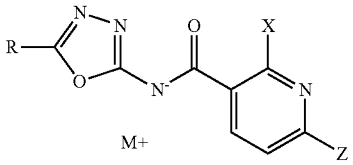

| No. | R | X | Z | $M^+$ | Physical data ($^1H$ NMR, DMSO-$d_6$, 400 MHz) |
|---|---|---|---|---|---|
| 2-2 | Me | Me | $CF_3$ | $Et_3N(Bn)^+$ | |
| 2-3 | Me | Me | $CF_3$ | $Pr_4N^+$ | 8.08 (d, 1H), 7.62 (d, 1H), 3.14-3.10 (m, 8H), 2.68 (s, 3H), 2.26 (s, 3H), 1.64-1.58 (m, 8H), 0.89 (t, 12H) |
| 2-4 | Me | Me | $CF_3$ | $Me_3N(CH_2CH_2OH)^+$ | 8.08 (d, 1H), 7.62 (d, 1H), 5.48 (bs, 1H), 3.85-3.82 (m, 2H), 3.41-3.38 (m, 2H), 3.10 (s, 12H), 2.68 (s, 3H), 2.27 (s, 3H) |
| 2-5 | Me | Me | $CF_3$ | $Me_3N(Bn)^+$ | 8.14 (d, 1H), 7.70 (d, 1H), 7.55-7.49 (m, 5H), 4.52 (s, 2H), 3.02 (s, 12H), 2.67 (s, 3H), 2.34 (s, 3H) |
| 2-6 | Me | Me | $CF_3$ | n-$Oct_4N^+$ | 8.08 (d, 1H), 7.62 (d, 1H), 3.17-3.13 (m, 8H), 2.68 (s, 3H), 2.26 (s, 3H), 1.62-1.49 (m, 8H), 1.32-1.18 (m, 40H), 0.86 (t, 12H) |
| 2-7 | Me | Me | $CF_3$ | $Et_3N(Bn)^+$ | 8.08 (d, 1H), 7.61 (d, 1H), 7.53-7.51 (m, 5H), 4.47 (s, 2H(, 3.16 (q, 8H), 2.68 (s, 3H), 2.26 (s, 3H), 1.30 (t, 12H) |
| 2-8 | Me | Me | $CF_3$ | $K^+$ | 8.13 (d, 1H), 7.68 (d, 1H), 2.68 (s, 3H), 2.33 (s, 3H) |
| 2-9 | Me | Me | $CF_3$ | $Li^+$ | 8.26 (d, 1H), 7.70 (d, 1H), 2.75 (s, 3H), 2.34 (s, 3H) |
| 2-10 | Me | Me | $CF_3$ | $Mg^{2+}$ | |
| 2-11 | Me | Me | $CF_3$ | $Ca^{2+}$ | |
| 2-12 | Me | Me | $CF_3$ | $Me_3S^+$ | |
| 2-13 | Me | Me | $CF_3$ | $Et_3S^+$ | |
| 2-14 | Me | Me | $CF_3$ | $Me_4N^+$ | 8.20 (d, 1H), 7.80 (d, 1H), 3.10 (s, 12H), 2.66 (s, 3H), 2.42 (s, 3H) |
| 2-15 | Me | Me | $CF_3$ | $Et_4N^+$ | 8.13 (d, 1H), 7.69 (d, 1H), 3.20 (q, 8H), 2.67 (s, 3H), 2.32 (s, 3H), 1.16 (t, 12H) |
| 2-16 | Me | Me | $CF_3$ | $Bu_4N^+$ | |
| 2-17 | Me | Me | $CF_3$ | i-$Pr_4N^+$ | |
| 2-18 | Me | Cl | $CF_3$ | $Na^+$ | |
| 2-19 | Me | Cl | $CF_3$ | $Pr_4N^+$ | |
| 2-20 | Me | Br | $CF_3$ | $Na^+$ | |
| 2-21 | Me | $CH_2OMe$ | $CF_3$ | $Na^+$ | |

B. FORMULATION EXAMPLES a) A dusting product is obtained by mixing 10 parts by weight of a compound of the formula (I) and/or salts thereof and 90 parts by weight of talc as an inert substance and comminuting the mixture in a hammer mill.

b) A readily water-dispersible, wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277 C), and grinding the mixture in a friction ball mill to a fineness of below 5 microns.

d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.

e) Water-dispersible granules are obtained by mixing 75 parts by weight of a compound of the formula (I) and/or salts thereof, 10 parts by weight of calcium lignosulfonate, 5 parts by weight of sodium lauryl sulfate, 3 parts by weight of polyvinyl alcohol and 7 parts by weight of kaolin, grinding the mixture in a pinned-disk mill, and granulating the powder in a fluidized bed by spray application of water as a granulating liquid.

f) Water-dispersible granules are also obtained by homogenizing and precomminuting, in a colloid mill, 25 parts by weight of a compound of the formula (I) and/or salts thereof, 5 parts by weight of sodium 2,2'-dinaphthylmethane-6,6'-disulfonate 2 parts by weight of sodium oleoylmethyltaurate, 1 part by weight of polyvinyl alcohol 17 parts by weight of calcium carbonate and 50 parts by weight of water, then grinding the mixture in a bead mill and atomizing and drying the resulting suspension in a spray tower by means of a one-phase nozzle.

C. BIOLOGICAL EXAMPLES

1. Pre-Emergence Herbicidal Action Against Harmful Plants

Seeds of monocotyledonous and dicotyledonous weed plants and crop plants are laid out in wood-fiber pots in sandy loam and covered with soil. The compounds of the invention and, for comparative purposes, the most structurally similar compounds known from WO 2012/126932 A1, formulated in the form of wettable powders (WP) or as emulsion concentrates (EC), are then applied to the surface of the covering soil as aqueous suspension or emulsion at a water application rate equating to 600 to 800 l/ha with addition of 0.2% of wetting agent. After the treatment, the pots are placed in a greenhouse and kept under good growth conditions for the trial plants. The damage to the test plants is scored visually after a test period of 3 weeks by comparison with untreated controls (herbicidal activity in percent (%): 100% activity=the plants have died, 0% activity=like control plants). The tested compounds of the invention exhibit better efficacy with respect to weed plants and simultaneously better compatibility, i.e. lower damage to crop plants. The comparative tests were conducted by way of example on some weed plants and crop plants.

The abbreviations used here are:

| | | | |
|---|---|---|---|
| ABUTH | Abutilon theophrasti | AMARE | Amaranthus retroflexus |
| POLCO | Polygonum convolvulus | | |
| TRZAS | Triticum aestivum (wheat) | STEME | Stellaria media |
| | | ZEAMX | Zea mays (corn) |

TABLE V1

| Compound No. | Dosage [g/ha] | Activity against ABUTH | Damage to TRZAS |
|---|---|---|---|
| 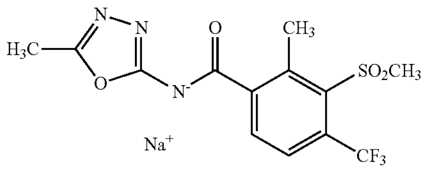 No. 1-14, inventive | 20 | 100% | 0% |
| 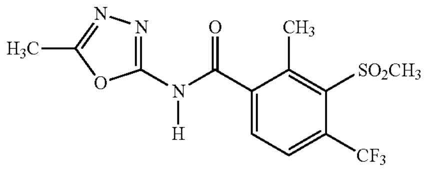 No. 2-145, from WO 2012/126932 | 20 | 70% | 40% |

TABLE V2

| Compound No. | Dosage [g/ha] | Activity against STEME | Damage to TRZAS |
|---|---|---|---|
| 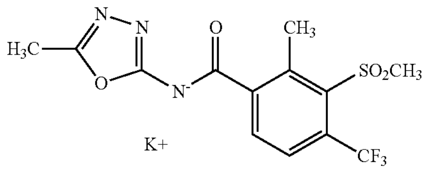 No. 1-16, inventive | 20 | 90% | 0% |
| 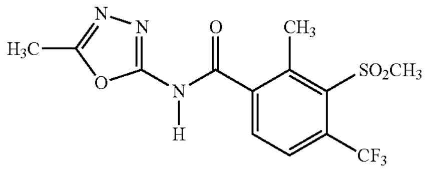 No. 2-145, from WO 2012/126932 | 20 | 70% | 40% |

TABLE V3
| Compound No. | Dosage [g/ha] | Activity against STEME | Damage to TRZAS |
|---|---|---|---|
| 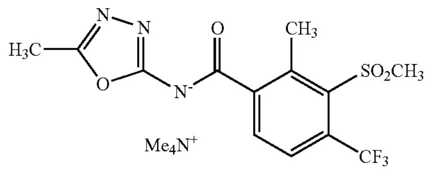 No. 1-21, inventive | 20 | 90% | 0% |
| 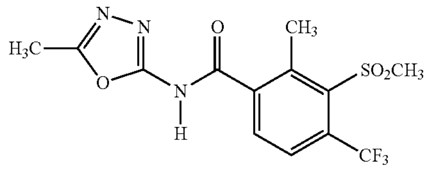 No. 2-145, from WO 2012/126932 | 20 | 70% | 40% |
TABLE V4
| Compound No. | Dosage [g/ha] | Activity against ABUTH | Damage to TRZAS |
|---|---|---|---|
| 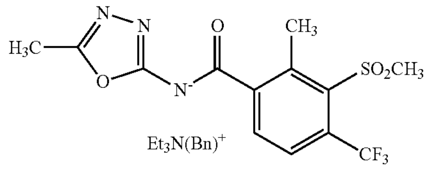 No. 1-25, inventive | 20 | 100% | 0% |
| 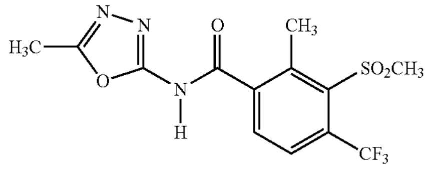 No. 2-145, from WO 2012/126932 | 20 | 70% | 40% |
TABLE V5
| Compound No. | Dosage [g/ha] | Activity against ABUTH | Damage to TRZAS |
|---|---|---|---|
| 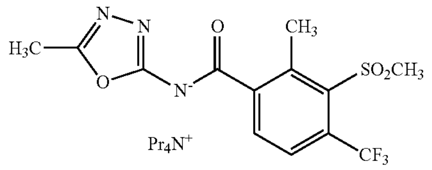 No. 1-26, inventive | 20 | 100% | 0% |

TABLE V5-continued
| Compound No. | Dosage [g/ha] | Activity against ABUTH | Damage to TRZAS |
|---|---|---|---|
| 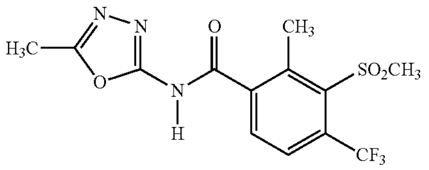 [SMILES: Cc1nnc(NC(=O)c2ccc(C(F)(F)F)c(S(C)(=O)=O)c2C)o1] No. 2-145, from WO 2012/126932 | 20 | 70% | 40% |
TABLE V6
| Compound No. | Dosage [g/ha] | Activity against ABUTH | Damage to TRZAS |
|---|---|---|---|
| 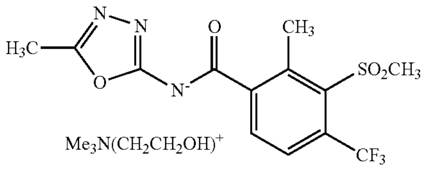 No. 1-27, inventive | 20 | 100% | 0% |
| 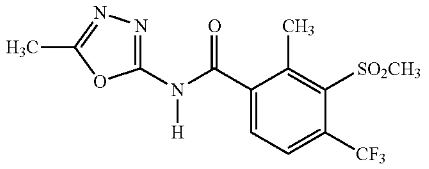 No. 2-145, from WO 2012/126932 | 20 | 70% | 40% |
TABLE V7
| Compound No. | Dosage [g/ha] | Activity against ABUTH | Damage to TRZAS |
|---|---|---|---|
| 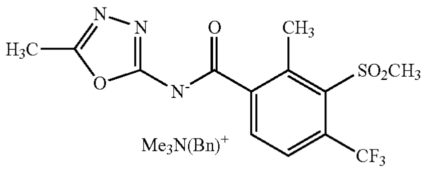 No. 1-28, inventive | 20 | 100% | 0% |
| 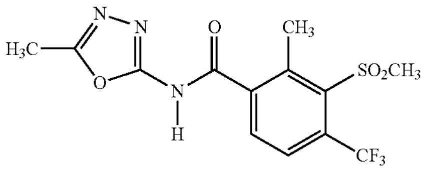 No. 2-145, from WO 2012/126932 | 20 | 70% | 40% |

TABLE V8
| Compound No. | Dosage [g/ha] | Activity against ABUTH | Damage to TRZAS |
|---|---|---|---|
| 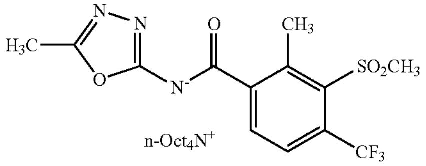 No. 1-29, inventive | 20 | 100% | 0% |
| 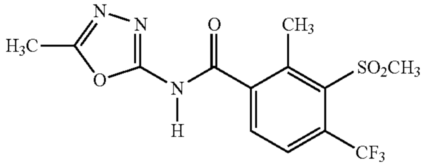 No. 2-145, from WO 2012/126932 | 20 | 70% | 40% |
TABLE V9
| | Dosage | Activity against | | | Damage to |
|---|---|---|---|---|---|
| Compound No. | [g/ha] | ALOMY | CYPES | ABUTH | ZEAMX |
| 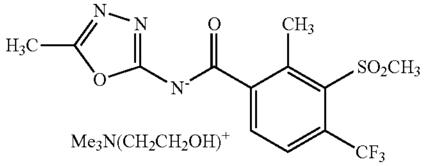 No. 1-27, inventive | 20 | 70% | 70% | 100% | 0% |
| 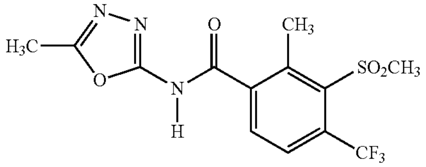 No. 2-145, from WO 2012/126932 | 20 | 20% | 40% | 70% | 0% |
TABLE V10
| | Dosage | Activity against | | | Damage to |
|---|---|---|---|---|---|
| Compound No. | [g/ha] | ALOMY | CYPES | ABUTH | ZEAMX |
| 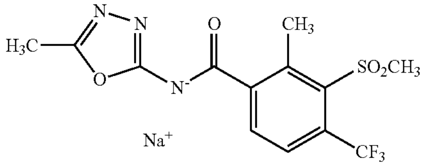 No. 1-14, inventive | 20 | 60% | 40% | 100% | 0% |

TABLE V10-continued
| Compound No. | Dosage [g/ha] | Activity against ALOMY | CYPES | ABUTH | Damage to ZEAMX |
|---|---|---|---|---|---|
| 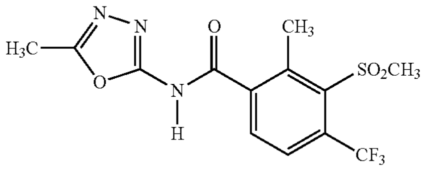 No. 2-145, from WO 2012/126932 | 20 | 20% | 40% | 70% | 0% |
TABLE V11
| Compound No. | Dosage [g/ha] | Activity against ALOMY | CYPES | ABUTH | Damage to ZEAMX |
|---|---|---|---|---|---|
| 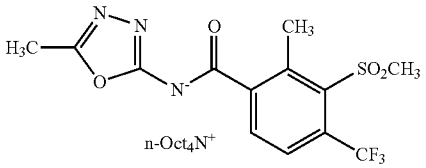 No. 1-29, inventive | 20 | 60% | 60% | 100% | 0% |
| 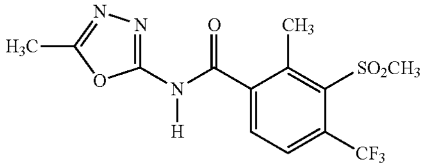 | 20 | 20% | 40% | 70% | 0% |
TABLE V12
| Compound No. | Dosage [g/ha] | Activity against ALOMY | CYPES | ABUTH | Damage to ZEAMX |
|---|---|---|---|---|---|
| 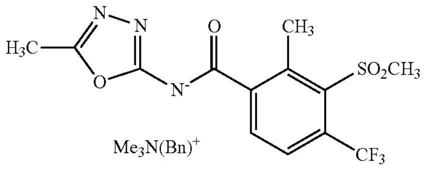 No. 1-28, inventive | 20 | 10% | 70% | 100% | 0% |
| 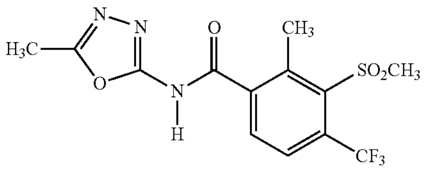 No. 2-145, from WO 2012/126932 | 20 | 20% | 40% | 70% | 0% |

TABLE V13
| Compound No. | Dosage [g/ha] | Activity against ALOMY | CYPES | ABUTH | Damage to ZEAMX |
|---|---|---|---|---|---|
| 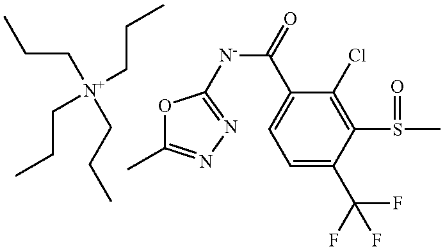 No. 1-152, inventive | 20 | 0% | 80% | 90% | 0% |
| 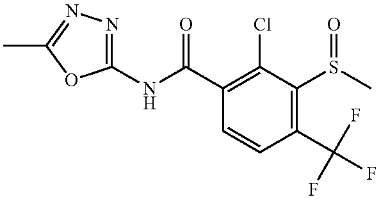 No. 2-360, from WO 2012/126932 | 20 | 20% | 60% | 60% | 0% |
TABLE V14
| Compound No. | Dosage [g/ha] | Activity against ALOMY | CYPES | ABUTH | Damage to ZEAMX |
|---|---|---|---|---|---|
| 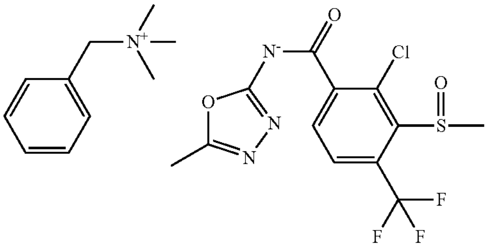 No. 1-154, inventive | 20 | 60% | 80% | 90% | 0% |
| 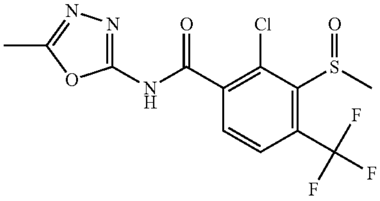 No. 2-360, from WO 2012/126932 | 20 | 20% | 60% | 60% | 0% |

TABLE V15

| Compound No. | Dosage [g/ha] | Activity against ALOMY | CYPES | ABUTH | Damage to ZEAMX |
|---|---|---|---|---|---|
| 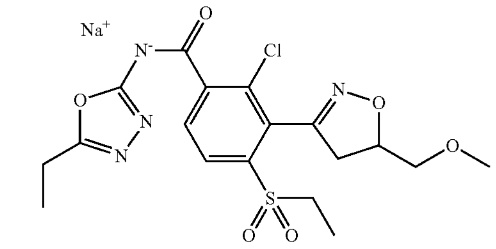 No. 1-243, inventive | 320 | 30% | 80% | 90% | 0% |
| 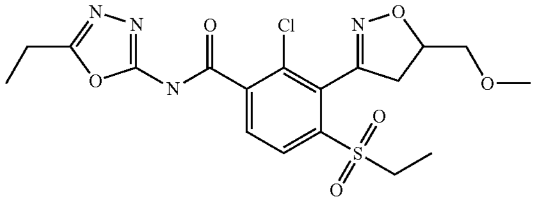 No. 3-265, from WO 2012/126932 | 320 | 10% | 80% | 90% | 0% |

TABLE V16

| Compound No. | Dosage [g/ha] | Activity against ALOMY | CYPES | ABUTH | Damage to ZEAMX |
|---|---|---|---|---|---|
| 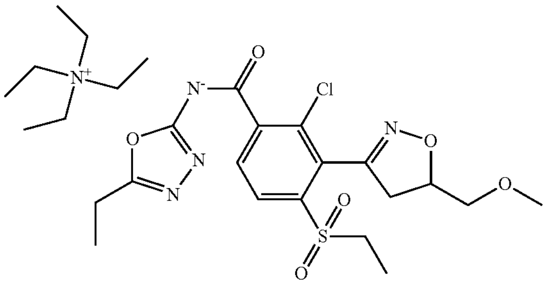 No. 1-244, inventive | 320 | 20% | 100% | 80% | 10% |
| 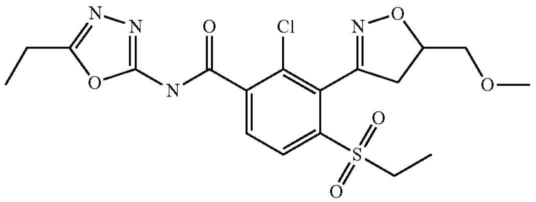 No. 3-265, from WO 2012/126932 | 320 | 10% | 80 | 10% | 0% |

2. Post-Emergence Herbicidal Action Against Harmful Plants

Seeds of monocotyledonous and dicotyledonous weed and crop plants are laid out in sandy loam in wood-fiber pots, covered with soil and cultivated in a greenhouse under good growth conditions. 2 to 3 weeks after sowing, the test plants are treated at the one-leaf stage. The compounds of the invention and, for comparative purposes, the most structurally similar compounds known from WO 2012/126932 A1, formulated in the form of wettable powders (WP) or as emulsion concentrates (EC), are then sprayed onto the green parts of the plants as aqueous suspension or emulsion at a water application rate equating to 600 to 800 l/ha with addition of 0.2% wetting agent. After the test plants have been left to stand in the greenhouse under optimal growth conditions for about 3 weeks, the action of the preparations is assessed visually in comparison to untreated controls (herbicidal action in percent (%): 100% activity=the plants have died, 0% activity=like control plants). The tested compounds of the invention exhibit better efficacy with respect to weed plants and simultaneously better compatibility, i.e. lower damage to crop plants. The comparative tests were conducted by way of example on some weed plants and crop plants.

TABLE N1

| Compound No. | Dosage [g/ha] | Activity against AMARE | Damage to ZEAMX |
|---|---|---|---|
| 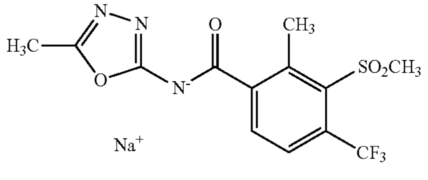 No. 1-14, inventive | 5 | 100% | 0% |
| 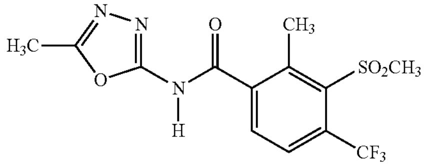 No. 2-145, from WO 2012/126932 | 5 | 80% | 40% |

TABLE N2

| Compound No. | Dosage [g/ha] | Activity against AMARE | Damage to ZEAMX |
|---|---|---|---|
| 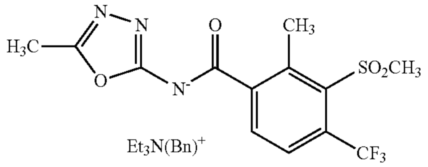 No. 1-25, inventive | 5 | 100% | 0% |
| 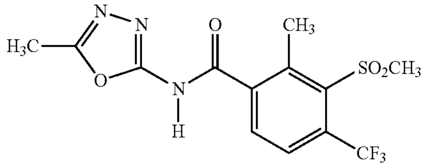 No. 2-145, from WO 2012/126932 | 5 | 80% | 40% |

TABLE N3

| Compound No. | Dosage [g/ha] | Activity against AMARE | Damage to ZEAMX |
|---|---|---|---|
| 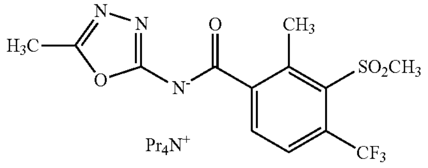 No. 1-26, inventive | 5 | 100% | 0% |

TABLE N3-continued
| Compound No. | Dosage [g/ha] | Activity against AMARE | Damage to ZEAMX |
|---|---|---|---|
| 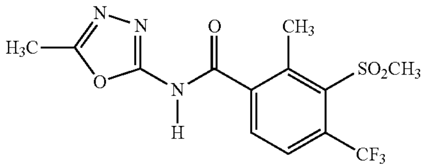 No. 2-145, from WO 2012/126932 | 5 | 80% | 40% |
TABLE N4
| Compound No. | Dosage [g/ha] | Activity against AMARE | Damage to ZEAMX |
|---|---|---|---|
| 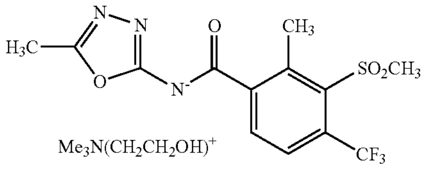 No. 1-27, inventive | 5 | 100% | 0% |
| 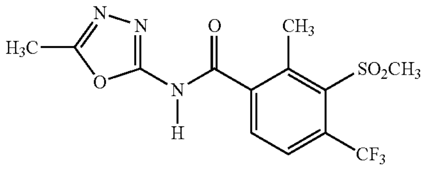 No. 2-145, from WO 2012/126932 | 5 | 80% | 40% |
TABLE N5
| Compound No. | Dosage [g/ha] | Activity against AMARE | Damage to ZEAMX |
|---|---|---|---|
| 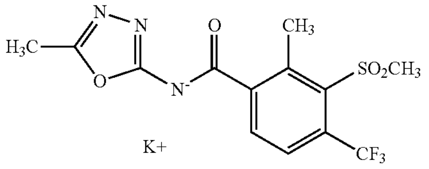 No. 1-16, inventive | 5 | 60% | 0% |
| 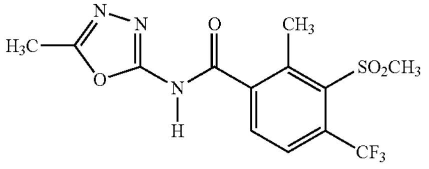 No. 2-145, from WO 2012/126932 | 5 | 40% | 40% |

TABLE N6
| Compound No. | Dosage [g/ha] | Activity against AMARE | Damage to ZEAMX |
|---|---|---|---|
| 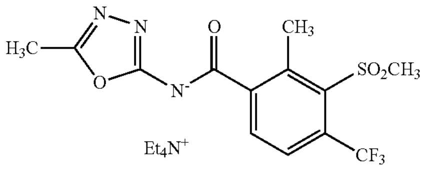 No. 1-22, inventive | 5 | 60% | 0% |
| 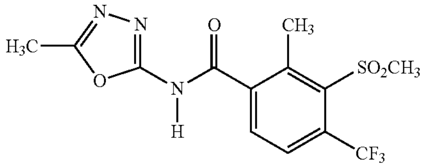 No. 2-145, from WO 2012/126932 | 5 | 40% | 40% |
TABLE N7
| | Dosage | Activity against | | Damage to |
|---|---|---|---|---|
| Compound No. | [g/ha] | ALOMY | VERPE | TRZAS |
| 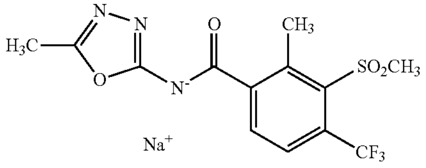 No. 1-14, inventive | 5 | 80% | 100% | 0% |
| 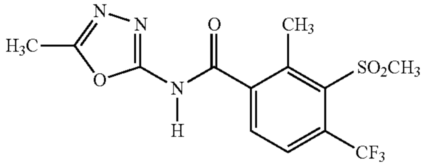 No. 2-145, from WO 2012/126932 | 5 | 60 | 60% | 80% |
TABLE N8
| | Dosage | Activity against | | Damage to |
|---|---|---|---|---|
| Compound No. | [g/ha] | ALOMY | VERPE | TRZAS |
| 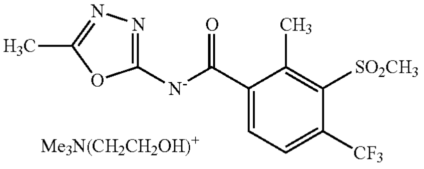 No. 1-27, inventive | 5 | 80% | 90% | 0% |

TABLE N8-continued
| Compound No. | Dosage [g/ha] | Activity against ALOMY | Activity against VERPE | Damage to TRZAS |
|---|---|---|---|---|
| 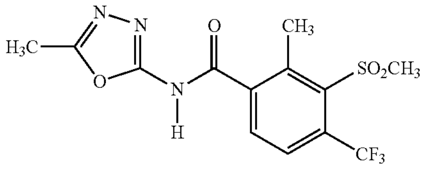 No. 2-145, from WO 2012/126932 | 5 | 60% | 60% | 80% |
TABLE N9
| Compound No. | Dosage [g/ha] | Activity against ALOMY | Activity against VERPE | Damage to TRZAS |
|---|---|---|---|---|
| 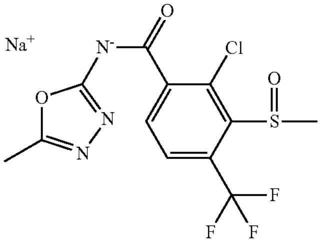 No. 1-150, inventive | 5 | 80% | 70% | 0% |
| 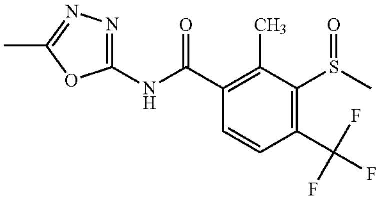 No. 2-360, from WO 2012/126932 | 5 | 60% | 50% | 30% |
TABLE N10
| Compound No. | Dosage [g/h] | Activity against ALOMY | Activity against VERPE | Damage to TRZAS |
|---|---|---|---|---|
| 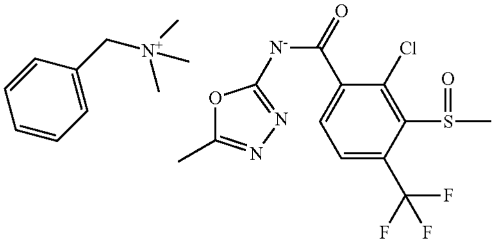 No. 1-154, inventive | 5 | 80% | 80% | 0% |

TABLE N10-continued

| Compound No. | Dosage [g/h] | Activity against ALOMY | Activity against VERPE | Damage to TRZAS |
|---|---|---|---|---|
| 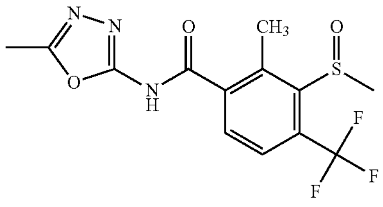 No. 2-360, from WO 2012/126932 | 5 | 60% | 50% | 30% |

The invention claimed is:

1. A salt of a N-(1,3,4-oxadiazol-2-yl)benzamide of formula (I)

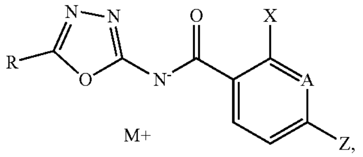

(I)

wherein

A is CY,

R is hydrogen or ($C_1$-$C_6$)-alkyl,

X is halogen, ($C_1$-$C_6$)-alkyl, or halo-($C_1$-$C_6$)-alkyl,

Y is $S(O)_nR^2$ or 4,5-dihydro-1,2-oxazol-3-yl substituted by ($C_1$-$C_6$)-alkoxy-($C_1$-$C_4$)-alkyl, Z is halo-($C_1$-$C_6$)-alkyl or $S(O)_nR^2$, or Z is optionally also hydrogen if Y is $S(O)_nR^2$, $R^2$ is ($C_1$-$C_6$)-alkyl, n is 1 or 2, and $M^+$ is a cation selected from the group consisting of sodium ion, potassium ion, lithium ion, $NH_4^+$ ion, tetra-N,N,N,N-(2-hydroxyeth-1-yl)ammonium ion, N-(2-hydroxyeth-1-yl)-tris-N,N,N-methylammonium ion, tetramethylammonium ion, tetraethylammonium ion, tetrapropylammonium ion, tetrabutylammonium ion, tetraoctyl-ammonium ion, trimethylbenzylammonium ion, and triethylbenzylammonium ion.

2. The salt of the N-(1,3,4-oxadiazol-2-yl)benzamide as claimed in claim 1, wherein A is CY, R is ($C_1$-$C_6$)-alkyl, X is halogen, ($C_1$-$C_6$)-alkyl, or halo-($C_1$-$C_6$)-alkyl, Y is $S(O)_nR^2$, Z is halo-($C_1$-$C_6$)-alkyl or $S(O)_nR^2$, $R^2$ is ($C_1$-$C_6$)-alkyl, n is 1 or 2, and M+ is a cation selected from the group consisting of sodium ion, potassium ion, lithium ion, and $NH_4^+$ ion.

3. The salt of the N-(1,3,4-oxadiazol-2-yl)benzamide as claimed in claim 1, wherein A is CY, R is methyl, X is methyl, Y methylsulfonyl, Z trifluoromethyl, M+ is a cation selected from the group consisting of sodium ion, potassium ion, $NH_4$±ion, N-(2-hydroxyeth-1-yl)-tris-N,N,N-methylammonium ion, tetramethylammonium ion, tetrapropylammonium ion, tetraoctylammonium ion, and trimethylbenzylammonium ion.

4. The salt of the N-(1,3,4-oxadiazol-2-yl)benzamide according to claim 3, wherein M+ is a sodium ion.

5. The salt of the N-(1,3,4-oxadiazol-2-yl)benzamide as claimed in claim 1, wherein A is CY and (a) R is $CH_3$, X is $CH_3$, Y is $S(O)_2CH_3$, Z is $CF^3$, and M+ is $N^+$;

(b) R is $CH_3$, X is $CH_3$, Y is $S(O)_2CH_3$, Z is $CF^3$, and M+ is $K^+$;

(c) R is $CH_3$, X is $CH_3$, Y is $S(O)_2CH_3$, Z is $CF^3$, and M+ is $(CH_3)_4N^+$;

(d) R is $CH_3$, X is $CH_3$, Y is $S(O)_2CH_3$, Z is $CF_3$, and M+ is $(CH_3CH_2)_4N^+$;

(e) R is $CH_3$, X is $CH_3$, Y is $S(O)_2CH_3$, Z is $CF^3$, and M+ is $(CH_3CH_2)_3N(benzyl)^+$;

(f) R is $CH_3$, X is $CH_3$, Y is $S(O)_2CH_3$, Z is $CF^3$, and M+ is $(propyl)_4N^+$;

(g) R is $CH_3$, X is $CH_3$, Y is $S(O)_2CH_3$, Z is $CF^3$, and M+ is $(CH_3)_3N(CH_2CH_2OH)^+$;

(h) R is $CH_3$, X is $CH_3$, Y is $S(O)_2CH_3$, Z is $CF^3$, and M+ is $(CH_3)_3N(benzyl)^+$;

(i) R is $CH_3$, X is $CH_3$, Y is $S(O)_2CH_3$, Z is $CF^3$, and M+ is $(n\text{-}octyl)_4N^+$;

(j) R is $CH_3$, X is Cl, Y is $S(O)CH_3$, Z is $CF^3$, and M+ is $N^+$;

(k) R is $CH_3$, X is Cl, Y is $S(O)CH_3$, Z is $CF^3$, and M+ is $(propyl)_4N^+$;

(l) R is $CH_3$, X is Cl, Y is $S(O)CH_3$, Z is $CF^3$, and M+ is $(CH_3)_3N(benzyl)^+$;

(m) R is $CH_3CH_2$, X is Cl, Y is 5-methoxymethyl-4,5-dihydro-1,2-oxazol-3-yl, Z is $S(O)_2CH_2CH_3$, and M+ is $N^+$; and (n) R is $CH_3CH_2$, X is Cl, Y is 5-methoxymethyl-4,5-dihydro-1,2-oxazol-3-yl, Z is $S(O)_2CH_2CH_3$, and M+ is $(CH_3CH_2)_4N^+$.

6. A herbicidal composition comprising a herbicidally active content of at least one compound of formula (I) as claimed in claim 1.

7. The herbicidal composition as claimed in claim 6 in a mixture with one or more formulation auxiliaries.

8. The herbicidal composition as claimed in claim 6, additionally comprising at least one further pesticidally active substance selected from the group consisting of insecticides, acaricides, herbicides, fungicides, safeners, and growth regulators.

9. The herbicidal composition as claimed in claim 8, wherein at least one further pesticidally active substance is a safener.

10. The herbicidal composition as claimed in claim 9, wherein the safener is cyprosulfamide, cloquintocet-mexyl, mefenpyr-diethyl or isoxadifen-ethyl.

11. The herbicidal composition as claimed in claim 8, additionally comprising a further herbicide.

12. A method of controlling unwanted plants, comprising applying an effective amount of at least one compound of formula (I) as claimed in claim 1 to the unwanted plants or to the site of the unwanted plants.

13. The method of claim 12, comprising applying an effective amount of at least one compound of formula (I) to unwanted plants in crops of useful plants.

14. The method of claim 13, wherein the useful plants are transgenic useful plants.

15. A method of controlling unwanted plants, comprising applying an effective amount of the herbicidal composition of claim 6 to the unwanted plants or to the site of the unwanted plants.

16. The method of claim 15, comprising applying an effective amount of the herbicidal composition to unwanted plants in crops of useful plants.

17. The method of claim 16, wherein the useful plants are transgenic useful plants.

* * * * *